United States Patent
Elliott et al.

(10) Patent No.: US 6,946,554 B2
(45) Date of Patent: Sep. 20, 2005

(54) PROCESS FOR THE PREPARATION OF 9-DEAZAGUANINE DERIVATIVES

(75) Inventors: Arthur J. Elliott, Aiken, SC (US); David A. Walsh, Birmingham, AL (US); Philip E. Morris, Birmingham, AL (US)

(73) Assignee: BioCryst Pharmaceuticals, Inc., Birmingham, AL (US)

( * ) Notice: Subject to any disclaimer, the term of this patent is extended or adjusted under 35 U.S.C. 154(b) by 0 days.

(21) Appl. No.: 10/878,035

(22) Filed: Jun. 29, 2004

(65) Prior Publication Data

US 2004/0254181 A1 Dec. 16, 2004

Related U.S. Application Data

(63) Continuation of application No. 08/762,832, filed on Dec. 10, 1996, now abandoned.

(51) Int. Cl.$^7$ ................. C07D 487/04; C07D 207/34

(52) U.S. Cl. ................. 544/280; 548/532

(58) Field of Search .................. 544/280

(56) References Cited

U.S. PATENT DOCUMENTS 5,554,615 A * 9/1996 Nomura et al. ............ 544/280
6,043,365 A * 3/2000 McQuire et al. ........... 544/280

* cited by examiner

*Primary Examiner*—Mark L. Berch
(74) *Attorney, Agent, or Firm*—Connolly, Bove, Lodge & Hutz, LLP

(57) ABSTRACT

Derivatives of 9-deazaguanine of the formula I:

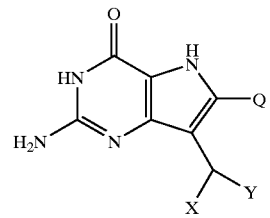

are prepared by reacting an aldehyde or ketone of the formula II:

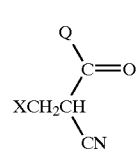

with a dialkylaminomalonate to produce an enamine. The enamine is then reacted with a base to produce a pyrrole represented by the formula:

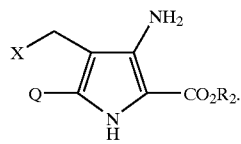

The pyrrole is reacted with a compound represented by the formula $R_3OC(O)N=C(Z)NHC(O)OR_3$ or a derivative of carbamimidoic acid to provide a protected guanidine compound. The guanidine compound is converted to the desired deazaguanine by reaction with 1) trifluoroacetic acid or 2) $C_1$–$C_4$ alkoxide or alkali metal or alkaline earth metal hydroxide followed by neutralization with an acid.

13 Claims, 4 Drawing Sheets

PROCESS FOR THE PREPARATION OF 9-DEAZAGUANINE DERIVATIVES

This application is a continuation of Ser. No. 08/762,832, filed Dec. 10, 1996, now abandoned.

TECHNICAL FIELD

The present invention is concerned with a procedure for producing 9-deazaguanine derivatives. The process of the present invention provides an economical procedure to produce 9-deazaguanine derivatives in relatively high overall yields. The process of the present invention makes possible large scale production of the 9-deazaguanine derivatives.

BACKGROUND ART

Derivatives of 9-deazaguanines are known and include compounds having the following formula:

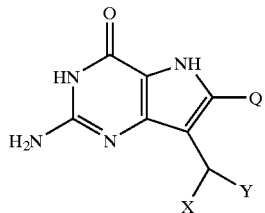

I wherein X can be a substituted or unsubstituted aryl ring, 5 or 6 member heterocyclic ring, alicyclic ring, or an alkyl group;
Y can be H, alkyl, $CH_2CN$, $CH_2CONH_2$, $CH_2CO_2H$, or $CH_2CO_2$ alkyl and Q can be H, alkyl, $CF_3$ or phenyl. For instance, see U.S. Pat. Nos. 4,923,872, 4,985,433, 4,985,434, 5,008,265, 5,008,270, and 5,189,039 and WO 90/10631, disclosures of which are incorporated herein by reference. Also, see Montgomery et al., J. Med. Chem. 1993, 36, 55–69.

Derivatives of 9-deazaguanine are useful as inhibitors of the enzyme purine nucleoside phosphorylase (PNP, EC 2.4.2.1) as discussed by Montgomery, Med. Res. Rev. 1933, 13, 209–228, and some have exhibited efficacy in clinical trials. For instance, see Montgomery et al., Drugs Future 1993, 18, 887–890. Various 9-deazaguanine derivatives also exhibit selective inhibition of T-cells and suppress cellular immunity. They can be used for treating autoimmune diseases, transplant rejection, psoriasis or gout in mammals. Moreover, certain of them potentiate the antiviral and anti-tumor effect of antiviral or antitumor purine nucleosides.

The synthesis of compounds of the above formula I has been previously approached by two pathways (Schemes I and II). The approach depicted in Scheme I (where Y=H) was described in U.S. Pat. No. 4,923,872 (see FIG. 1). However, it is not suitable for preparing the wide range of compounds depicted by the above formula I.

Scheme II (see FIG. 2) depicts the synthetic approach described by Montgomery et al., J. Med. Chem. 1993, 36, 55–59, which was based on Lim et al., J. Org. Chem., 1979, 44, 3826–3829; Lim et al., Tetrahedron Lett. 1981, 22, 25–28; and Lim et al., J. Org. Chem. 1983, 48, 780–788.

The procedure depicted in Scheme II suffers many drawbacks: the number of steps (10) involved led to poor overall yields; starting materials and reagents were very expensive, resulting in a procedure that was not economically feasible; several reagents were difficult to use and dangerous (pyrophoric, lachrymatory) on large scale; moisture had to be excluded on several steps, which is sometimes difficult on large scale; there were several isolations and manipulations (chromatography, pressure reaction) which were difficult on large scale; there was a relatively large usage of halogenated solvents on several steps, which poses a costly and environmentally unsound waste disposal problem.

Large quantities of the compounds of the above formula I have been desired for clinical studies. However, the procedures listed in both Schemes I and II are not appropriate for large-scale synthesis. Therefore, a new synthetic procedure was required to economically provide sufficient quantities of compounds of the above formula I.

SUMMARY OF INVENTION

The present invention provides a process for preparing 9-deazaguanine derivatives that represents a significant improvement over prior art methods. The process of the present invention is relatively easy to manipulate on a large scale, and gives a high overall yield of desired compound.

Moreover, the process of the present invention does not require halogenated solvents and does not require extreme temperatures or pressures. In particular, the process of the present invention is concerned with producing 9-substituted-9-deazaguanine derivatives of the formula:

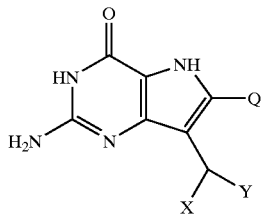

I wherein X is a member selected from the group consisting of substituted and unsubstituted aryl, 5 and 6 member heterocyclic rings, alicyclic rings, and groups represented by the formula:

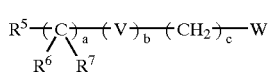

IA wherein $R_5$ is an optionally substituted cyclic group containing one or more heteroatoms,
$R_6$ and $R_7$ are each independently H or $C_{1-4}$ alkyl, a is 0–6, b is 0–6, c is 0–1, W is CN, $CSNH_2$, $PO(OH)_2$, COOH, $SO_2NH_2$, $NH_2$, OH, $CONHNH_2$, tetrazole, triazole, or $COR_8$ where $R_8$ is $C_{1-4}$ alkyl, $CF_3$, $NH_2$ or $OC_{1-4}$ alkyl, and V is O or NH.
Q is a member selected from the group consisting of hydrogen, $C_1-C_3$ alkyl, $CF_3$ and phenyl; and
Y is selected from the group consisting of: hydrogen, $C_1-C_4$ alkyl, $C_1-C_4$ alkyl CN, $C_1-C_4$ alkyl $CONH_2$, $C_1-C_4$ alkyl $CO_2H$, and $C_1-C_4$ alkyl $CO_2$ $C_1-C_4$ alkyl.

The process comprises reacting an aldehyde or ketone represented by the formula:

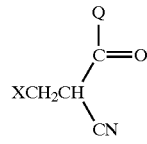

II wherein X and Q are the same as defined above in Formula I, with a di$C_1$–$C_4$ alkyl aminomalonate to provide an enamine represented by the formula:

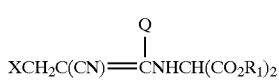

III wherein $R_1$ is a $C_1$–$C_4$ alkyl group, X and Q are the same as defined above for formula I.

The enamine III obtained above is reacted with a base to produce a cyclic pyrrole. The cyclic pyrrole is represented by the formula:

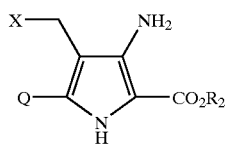

IV wherein X and Q are as defined above. $R_2$ is a $C_1$–$C_4$ alkyl group.

The cyclic pyrrole IV obtained from the above step is reacted with a urea compound or a derivative of carbamimidoic acid to provide a protected guanidino compound. The urea compound is represented by the formula:

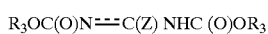

V $$R_3OC(O)N=C(Z)\,NHC(O)OR_3$$

wherein $R_3$ is $C_1$–$C_4$ alkyl and Z is a S alkyl of 1–4 carbon atoms, =S, S—H, Cl or $C_{1-4}$ alkoxy.

When reacting with the urea, the protected guanidino compound is represented by the formula

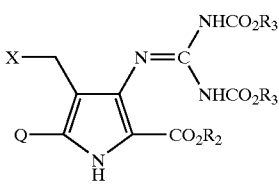

VI wherein X, Q and $R_2$ and $R_3$ are the same as defined above.

The protected guanidino compound is converted to the desired end product of formula I by reaction with trifluoroacetic acid. Alternatively, the protected guanidino compound is reacted with $C_1$–$C_4$ alkoxide, alkali metal hydroxide or alkaline earth metal hydroxide followed by neutralizing with an acid.

The derivative of carbamimidoic acid is represented by the formula

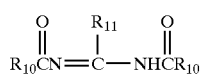

Va wherein each $R_{10}$ is individually a phenyl or phenyl substituted with one or more and more typically one of halogen such as chlorine, trifluoromethyl, nitro, $C_1$–$C_6$ alkyl or $C_1$–$C_3$ alkoxy; and $R_{11}$ is a $C_1$–$C_4$ alkoxy group.

In the case of using the derivative of carbamimidoic acid, the protected guanidino compound is represented by the formula

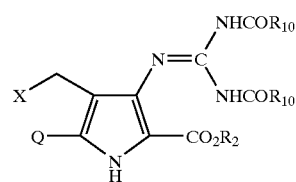

VIa

BEST AND VARIOUS MODES FOR CARRYING OUT INVENTION

Figure 1:
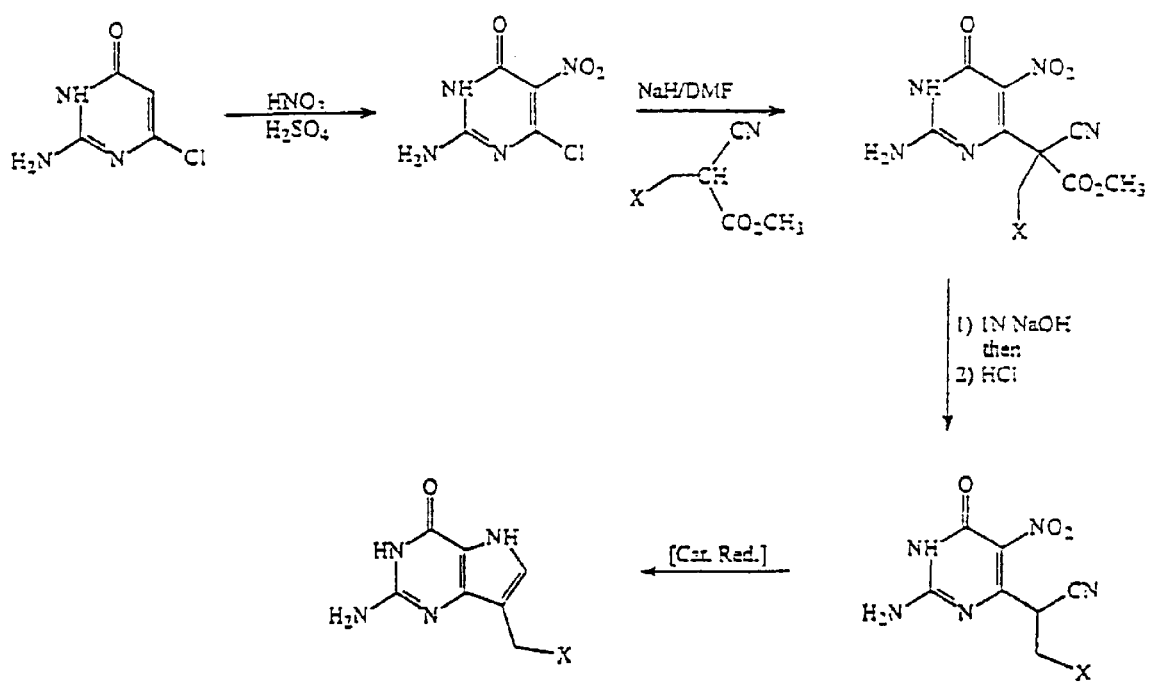
FIGS. 1 and 2 illustrate prior art methods for preparing certain 9-deazaguanine derivatives.
Figure 2:
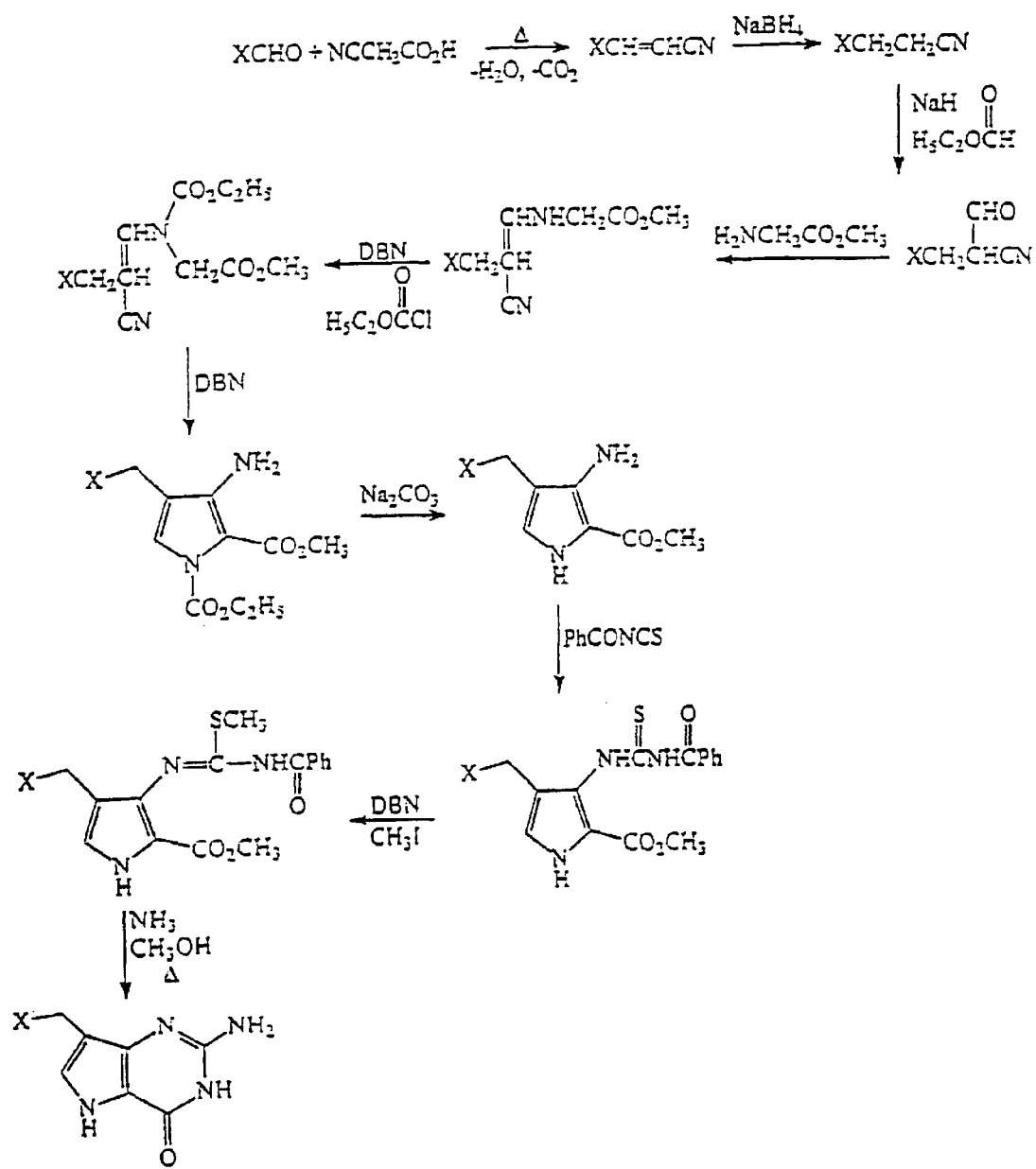
Figure 3:
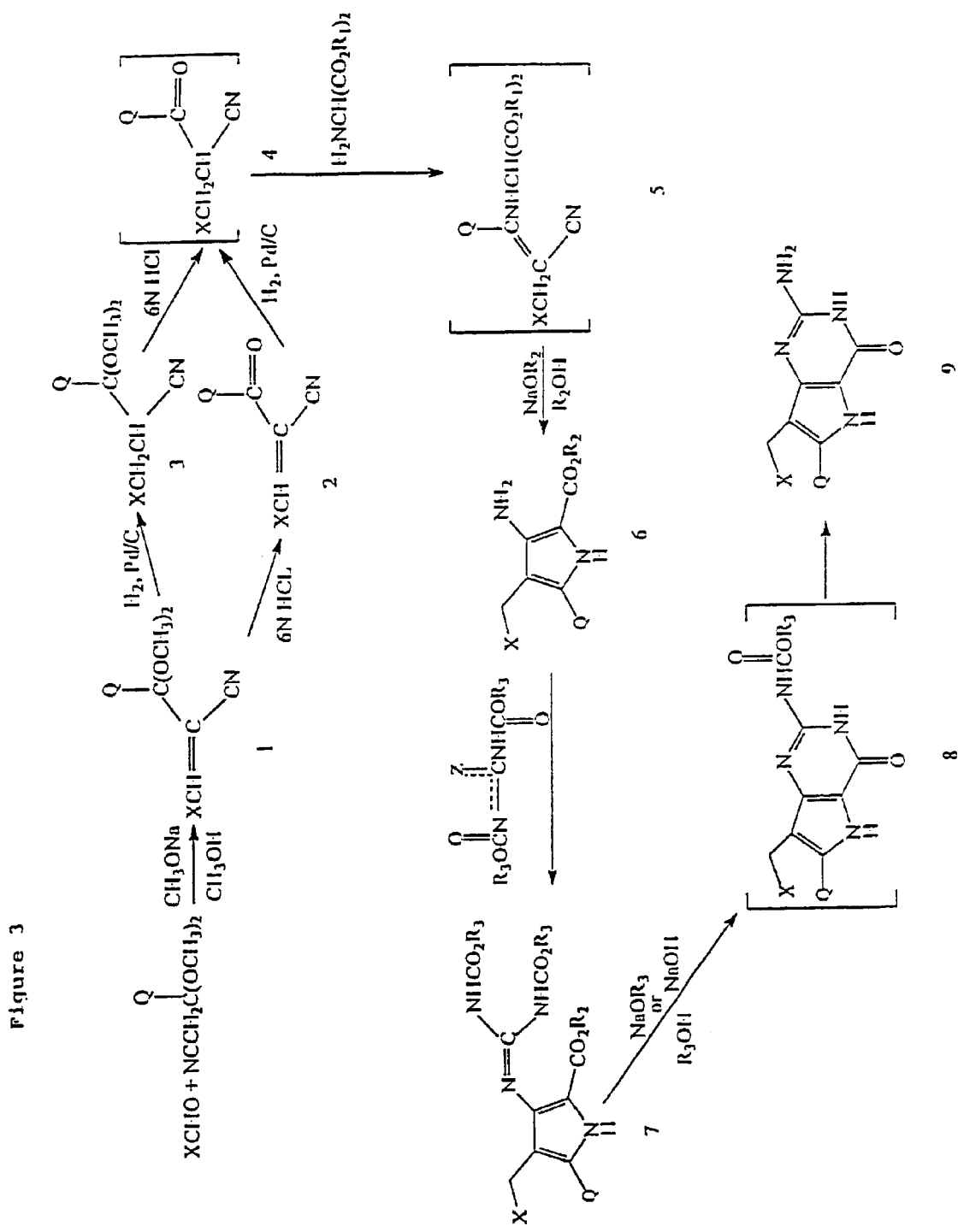
FIG. 3 illustrates a method of the present invention for producing 9-deazaguanine derivatives.
Figure 4:
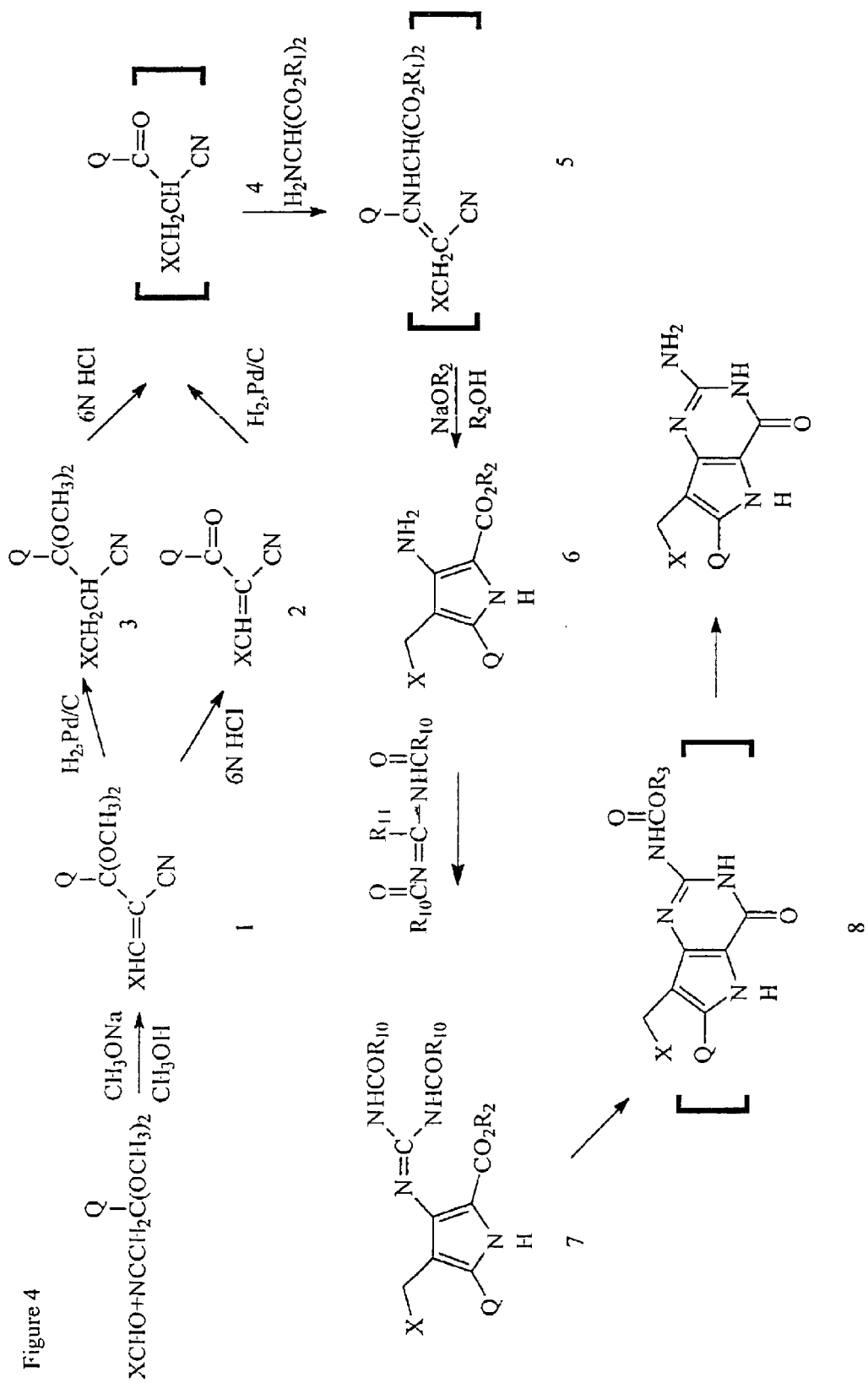
FIG. 4 illustrates an alternative method of the present invention for producing 9-deazaguanine derivatives.

The present invention is concerned with a process for producing 9-deazaguanine derivatives and especially 9-substituted-9-deazaguanine derivatives of the formula:

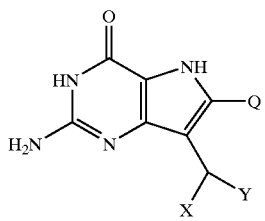

I

X in the above formula I can be a substituted or unsubstituted aryl group, 5 member heterocyclic ring, 6 member heterocyclic ring, alicyclic ring or group represented by the formula:

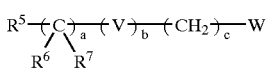

IA wherein $R_5$ is an optionally substituted cyclic group containing one or more heteroatoms, $R_6$ and $R_7$ are each independently H or $C_{1-4}$ alkyl, a is 0–6, b is 0–6, c is 0–1, W is CN, $CSNH_2$, $PO(OH)_2$, COOH, $SO_2NH_2$, $NH_2$, OH, $CONHNH_2$, tetrazole, triazole, or $COR_8$ where $R_8$ is $C_{1-4}$ alkyl, $CF_3$, $NH_2$ or $OC_{1-4}$ alkyl, and V is O or NH.

The substituted rings can include one or two substitutions that can be halogen, $C_1$–$C_3$ alkyl, $C_1$–$C_3$ alkoxy, benzyloxy, hydroxy and trifluoromethyl. Preferred aryl groups are phenyl and 1- or 2-naphthyl.

The heterocyclic rings contain one N, S or O atom as the hetero-atom in the ring. Typical 5 member heterocyclic rings include 2- or 3-furanyl, 2- or 3-thienyl, 2- or 3-tetrahydrofuranyl, 2- or 3-tetrahydrothienyl, and 2- or 3-pyrrolidinyl.

Typical 6 member heterocyclic rings include 2-, 3-, or 4-piperidinyl, 2-, 3-, or 4-tetrahydropyranyl, and 2-, 3-, or 4-pyridinyl.

Examples of alicyclic rings include cycloparaffins and cycloolefins. The cycloparaffins and cycloolefins preferably contain up to 9 carbon atoms in the structure. Preferred groups are single-ring cycloparaffins such as cyclopentyl, cyclohexyl, and cycloheptyl, multi-ring cycloparaffins such as 1- and 2-adamantyl, 1-norbornanyl, 2-exo-norbornanyl, 2-endo-norbornanyl, 1- and 2-bicyclo[2.2.2]octanyl, 1, 2-, 3-, 6- and 8-bicyclo[3.2.1]octanyl, and 1-, 2-, and 3-bicyclo [3.3.1]nonanyl and cycloolefins such as cyclohexenyl, 1- and 2-norbornenyl.

The optionally substituted cyclic group (hereinafter referred to as cyclo) recited for the above formula IA includes aromatic, heteroaromatic, alicyclic, and heteroalicyclic groups preferably containing five to nine atoms. Preferred optional substituents include halogen, hydroxy, alkoxy, alkyl, and trifluoromethyl. Exemplary substituents include chloro, fluoro, methoxy, ethoxy, propoxy, butoxy, methyl, ethyl, propyl and butyl. Preferred heteroatoms include oxygen, nitrogen, and sulfur, which can be present in combination in the same group. The preferred aromatic and heteroaromatic groups are phenyl, 2- or 3-thienyl, 2- or 3-furanyl, 2-, 3-, or 4-pyridinyl, 2- or 3-pyrrolyl, 2-, 4-, or 5-thiazolyl, 2-pyrazinyl, 3- or 4-pyridazinyl, and 3-, 4-, or 5-pyrazolyl. The preferred alicyclic and heteroalicyclic groups are 1- or 2-adamantyl, cyclohexyl, cycloheptyl, 2- or 3-tetrahydrofuranyl, 2- or 3-tetrahydrothienyl, 2- or 3-tetrahydropyranyl, 2-, 3-, or 4-piperidinyl, 3- or 4-pyrazolidinyl, 2-, 4-, or 5-thiazolidinyl, 2- or 3-piperazinyl, 2- or 3-morpholinyl, or 3- or 4-hexahydropyridazinyl.

Examples of preferred compounds prepared pursuant to the present invention are:

2-amino-7-(3-chlorophenylmethyl)-3H,5H-pyrrolo[3,2-d]pyrimidin-4-one;
2-amino-7-(4-benzyloxyphenylmethyl)-3H,5H-pyrrolo[3,2-d]pyrimidin-4-one;
2-amino-7-(3-benzyloxyphenylmethyl)-3H,5H-pyrrolo[3,2-d]pyrimidin-4-one;
2-amino-7-(phenylmethyl)-3H,5H-pyrrolo[3,2-d]pyrimidin-4-one;
2-amino-7-(4-chlorophenylmethyl)-3H,5H-pyrrolo[3,2-d]pyrimidin-4-one;
2-amino-7-(3-fluorophenylmethyl)-3H,5H-pyrrolo[3,2-d]pyrimidin-4-one;
2-amino-7-(3-methylphenylmethyl)-3H,5H-pyrrolo[3,2-d]pyrimidin-4-one;
2-amino-7-(3-methoxyphenylmethyl)-3H,5H-pyrrolo[3,2-d]pyrimidin-4-one;
2-amino-7-(3-trifluorophenylmethyl)-3H,5H-pyrrolo[3,2-d]pyrimidin-4-one;
2-amino-7-(3,4-dichlorophenylmethyl)-3H,5H-pyrrolo[3,2-d]pyrimidin-4-one;
2-amino-7-(2-furanylmethyl)-3H,5H-pyrrolo[3,2-d]pyrimidin-4-one;
2-amino-7-(2-thienylmethyl)-3H,5H-pyrrolo[3,2-d]pyrimidin-4-one;
2-amino-7-(3-thienylmethyl)-3H,5H-pyrrolo[3,2-d]pyrimidin-4-one;
2-amino-7-(2-chlorophenylmethyl)-3H,5H-pyrrolo[3,2-d]pyrimidin-4-one;
2-amino-7-(2-benzyloxyphenylmethyl)-3H,5H-pyrrolo[3,2-d]pyrimidin-4-one;
2-amino-7-(4-iodophenylmethyl)-3H,5H-pyrrolo[3,2-d]pyrimidin-4-one;
2-amino-7-(2-adamantylmethyl)-3H,5H-pyrrolo[3,2-d]pyrimidin-4-one;
2-amino-7-(1-adamantylmethyl)-3H,5H-pyrrolo[3,2-d]pyrimidin-4-one;
2-amino-7-(cyclopentylmethyl)-3H,5H-pyrrolo[3,2-d]pyrimidin-4-one;
2-amino-7-(cyclohexylmethyl)-3H,5H-pyrrolo[3,2-d]pyrimidin-4-one;
2-amino-7-(cycloheptylmethyl)-3H,5H-pyrrolo[3,2-d]pyrimidin-4-one;
2-amino-7-(1-norbornanylmethyl)-3H,5H-pyrrolo[3,2-d]pyrimidin-4-one;
2-amino-7-(2-exo-norbornanylmethyl)-3H,5H-pyrrolo[3,2-d]pyrimidin-4-one;
2-amino-7-(2-endo-norbornanylmethyl)-3H,5H-pyrrolo[3,2-d]pyrimidin-4-one;
2-amino-7-(1-norbornenymethyl)-3H,5H-pyrrolo[3,2-d]pyrimidin-4-one;
2-amino-7-(2-norbornenymethyl)-3H,5H-pyrrolo[3,2-d]pyrimidin-4-one;
2-amino-7-(1-bicyclo[2.2.2]-octanylmethyl)-3H,5H-pyrrolo[3,2-d]pyrimidin-4-one;
2-amino-7-(1-bicyclo[3.2.1]-octanylmethyl)-3H,5H-pyrrolo[3,2-d]pyrimidin-4-one;
2-amino-7-(1-bicyclo[3.3.1]nonanylmethyl)-3H,5H-pyrrolo[3,2-d]pyrimidin-4-one;
2-amino-7-(1-noradamantylmethyl)-3H,5H-pyrrolo[3,2-d]pyrimidin-4-one;
2-amino-7-(3-pyridinylmethyl)-3H,5H-pyrrolo[3,2-d]pyrimidin-4-one;
2-amino-7-(2-pyridinylmethyl)-3H,5H-pyrrolo[3,2-d]pyrimidin-4-one;
2-amino-7-(4-pyridinylmethyl)-3H,5H-pyrrolo[3,2-d]pyrimidin-4-one;
2-amino-7-(1-cyclohexenyl)-3H,5H-pyrrolo[3,2-d]pyrimidin-4-one;
2-amino-7-(2-cyclohexenyl)-3H,5H-pyrrolo[3,2-d]pyrimidin-4-one;
2-amino-7-(3-cyclohexenyl)-3H,5H-pyrrolo[3,2-d]pyrimidin-4-one;
2-amino-7-(cyclohexenyl)-3H,5H-pyrrolo[3,2-d]pyrimidin-4-one;
2-amino-7-(2-piperidinylmethyl)-3H,5H-pyrrolo[3,2-d]pyrimidin-4-one;
2-amino-7-(3piperidinylmethyl)-3H,5H-pyrrolo[3,2-d]pyrimidin-4-one;
2-amino-7-(4-piperidinylmethyl)-3H,5H-pyrrolo[3,2-d]pyrimidin-4-one;
2-amino-7-(2-tetrahydrofuranylmethyl)-3H,5H-pyrrolo[3,2-d]pyrimidin-4-one;
2-amino-7-(3-tetrahydrofuranylmethyl)-3H,5H-pyrrolo[3,2-d]pyrimidin-4-one;
2-amino-7-(2-tetrahydrothienylmethyl)-3H,5H-pyrrolo[3,2-d]pyrimidin-4-one;
2-amino-7-(3-tetrahydrothienylmethyl)-3,5H-pyrrolo[3,2-d]pyrimidin-4-one;
2-amino-7-(2-pyrrolidinylmethyl)-3H,5H-pyrrolo[3,2-d]pyrimidin-4-one;
2-amino-7-(3-pyrrolidinylmethyl)-3H,5H-pyrrolo[3,2-d]pyrimidin-4-one;
2-amino-7-(2-tetrahydropyranylmethyl)-3H,5H-pyrrolo[3,2-d]pyrimidin-4-one;
2-amino-7-(3-tetrahydropyranylmethyl)-3H,5H-pyrrolo[3,2-d]pyrimidin-4-one;
2-amino-7-(4-tetrahydropyranylmethyl)-3H,5H-pyrrolo[3,2-d]pyrimidin-4-one;

Q in the above formula I can be hydrogen, $C_1$–$C_3$ alkyl, $CF_3$ or phenyl and is preferably hydrogen.

Y in the above formula I can be: hydrogen, $C_1$–$C_4$ alkyl, $C_1$–$C_4$ alkyl CN, $C_1$–$C_4$ alkyl $CONH_2$, $C_1$–$C_4$ alkyl $CO_2H$, and $C_1$–$C_4$ alkyl $CO_2$ $C_1$–$C_4$ alkyl and is preferably H.

The process of the present invention comprises reacting an aldehyde or ketone represented by the formula:

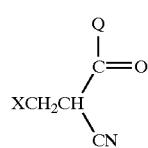

II wherein X and Q are the same as defined above for formula I, with $diC_1$–$C_4$ alkylaminomalonate to provide an enamine.

Examples of suitable dialkylaminomalonates are dimethylaminomalonate, diethylaminomalonate, dipropylaminomalonate and dibutylaminomalonate. In addition, the malonate can be a mixed malonate such as ethylmethyl aminomalonate. The preferred dialkylaminomalonate is diethyl aminomalonate.

The reaction is typically carried out at temperatures of about 20° C. to about 60° C., and preferably at normal room temperatures and atmospheric pressure. The reaction is typically carried out in an aqueous medium of water per se or water and an organic diluent such as a lower $C_1$–$C_4$ alcohol. The pH of this stage of the reaction is typically about 5 to about 8, and preferably about 6, and can be adjusted by adding an organic or inorganic acid, such as acetic acid or HCl.

The enamine obtained can be represented by the formula:

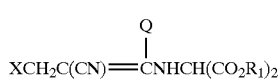

III wherein $R_1$ is a $C_1$–$C_4$ alkyl group, and X and Q are the same as defined above for formula I. $R_1$ is preferably ethyl.

Surprisingly, the enamine of formula III can be cyclized without requiring protecting the secondary nitrogen group.

The aldehydes and ketones of formula II can be prepared by several different methods. In particular, aldehydes represented by the formula XCHO are available commercially and/or can be produced by well known prior art procedures. The aldehyde XCHO is converted to an acetal or ketal by known condensation reactions, such as with 3,3-dimethoxypropionitrile under basic conditions as described by Manchand et al., J. Org. Chem., 1992, 57, 3531–3535.

If desired, the starting aldehyde and/or acetal can be purified by simple distillation. The acetal or ketal can be represented by the formula:

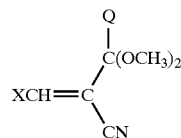

The acetal or ketal then can be treated to give the aldehyde of formula II. One method involves admixing the acetal and a strong acid, such as sulfuric acid, hydrochloric acid, phosphoric acid, trifluoracetic acid or methanesulfonic acid. The preferred acid is 6N hydrochloric acid. The amount of acid is used in excess.

The reaction results in producing a conjugated aldehyde or ketone having the formula:

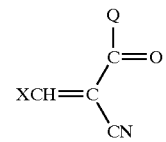

The conjugated aldehyde or ketone precipitates out and is isolated either as a crystalline solid or as an oil. The conjugated aldehyde or ketone is then reduced to the ketone or aldehyde of formula II, using for instance, hydrogen over a palladium or platinum catalyst supported on carbon.

In an alternative method, the acetal or ketal can be reduced employing a hydrogenation catalyst, such as platinum or palladium supported on carbon, or using sodium borohydride to produce an acetal or ketal represented by the formula:

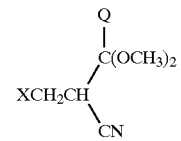

This compound is then converted to the aldehyde or ketone of formula II employing a strong acid, such as hydrochloric acid, phosphoric acid, trifluoroacetic acid, sulfuric acid or methanesulfonic acid, with 6N hydrochloric acid being preferred.

Furthermore, the aldehydes or ketones of formula II can be prepared by the methods described in U.S. Pat. No. 5,189,039, disclosure of which is incorporated herein by reference.

The process then involves reacting the enamine of formula III with a base to produce a cyclic pyrrole. Suitable bases include strong anhydrous bases, such as alkali metal and alkaline earth metal hydroxides, sodium hydride, and sodium amide, as well as organic bases, such as pyridine, triethylamine, 1,5-diazabicyclo[4.3.0]non-5-ene (DBN) and 1,8-diazabicyclo[5.4.0]-undec-7-ene (DBU).

The cyclization step is carried out in the presence of a lower $C_1$–$C_4$ alcohol, preferably methanol. The amount of base is typically about 1 to about 3 moles/mole enamine.

The temperature of this step of the process is usually about 20° to about 60°, and preferably normal room temperatures. This stage of the process is usually completed in about 1 to about 6 hours, and more typically about 2 to about 4 hours.

The cyclic pyrrole can be readily isolated by conventional means on a relatively large scale in excellent yields.

The cyclic pyrrole is then reacted with a urea compound to provide a protected guanidino compound, such as by the procedure described by Kim et al., Improved Method for the Preparation of Guanidines, Tetrahedron Letters, Volume 34, No. 48, pp. 7677–7680, 1993. In the alternative, the cyclic pyrrole can be reacted with a derivative of carbamimidoic acid to provide a protected guanidino compound.

The urea compound is represented by the following formula:

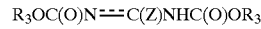

wherein $R_3$ is $C_1$–$C_4$ alkyl and Z is S alkyl 1–4 carbon atoms, =S, S—H, Cl, or $C_{1-4}$ alkoxy.

The derivatives of carbamimidoic acid are represented by the formula

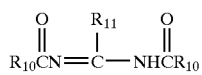

wherein $R_{10}$ is phenyl or phenyl substituted with one or more and more typically one of halogen such as chlorine, trifluoromethyl, nitro, $C_1$–$C_6$ alkyl or $C_1$–$C_3$ alkoxy; and $R_{11}$ is $C_{1-4}$ alkoxy group.

The protected guanidino compound in the case employing a urea compound is represented by the formula:

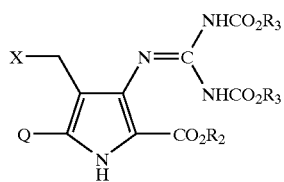

wherein X, Q and $R_2$ and $R_3$ are the same as defined above.

In the case employing a derivative of carbamimidoic acid, the protected guanidino compound is represented by the formula:

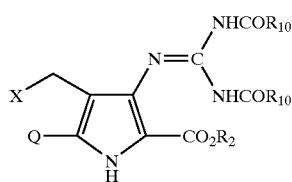

wherein X, Q, $R_2$ and $R_{10}$ are the same as defined above.

This condensation reaction can be carried out in the presence of a metal salt, or in the case when Z is S alkyl, in the presence of a weak acid. Suitable salts include mercuric chloride, mercuric iodide, cupric sulfate, zinc chloride, stannic chloride, silver nitrate, aluminum chloride, lead oxide, lead nitrate, ferric chloride, zinc fluoride, nickel fluoride and nickel chloride. Suitable weak acids include acetic acid, oxalic acid and succinic acid.

In addition, this reaction may be carried out in the presence of a base, such as those used in the cyclization step, and an organic solvent, such as acetonitrile.

The temperature is typically about 20° C. to about 100° C., and preferably at about normal room temperatures.

The protected S-alkylisothiourea derivatives are known and can be prepared using, for instance, the procedures described by Kruse et al., J. Med. Chem., 1989, 32, 409–417. In addition, the S-alkylisothioureas, if desired, can be converted to the more reactive chloro derivatives with sulfuryl chloride, as described by Saulnier et al., Biorg. and Med. Chem. Lett., 1994, 4, 1985–1990.

The protected urea derivatives wherein Z is $C_1$–$C_4$ alkoxy are known and can be prepared using the procedures described in Indian Patent Specification 1687842. The derivatives of carbamimidoic acid are known and can be prepared using the procedures described in U.S. Pat. No. 4,977,189 to Tomcufcik et al.

The protected guanidino compound can be directly converted to the desired 9-deazaguanidine derivative with trifluoroacetic acid in a solvent or neat. The amount of trifluoroacetic acid in a solvent is typically about 1 to about 10 molar excess, and more typically about 3 to about 5 molar excess. The reaction is typically carried out at temperatures of about 20° C. to about 60° C., and preferably normal room temperatures. The reaction usually takes about 1 to about 6 hours, and more usually about 2 to about 4 hours.

In the alternative, the protected guanidino compound can be converted to the desired end product of formula I by reacting with an alkoxide or hydroxide, followed by neutralizing with an acid. The alkoxide is typically a $C_1$–$C_4$ alkoxide and the hydroxide is an alkali metal hydroxide or alkaline earth metal hydroxide, with sodium hydroxide preferred.

The amount of the alkoxide or hydroxide is typically about 2 to about 10 molar excess, and more typically about 3 to about 5 molar excess.

Typical acids include weak acids, such as acetic acid, oxalic acid and succinic acid and strong acids, such as hydrochloric acid and sulfuric acid.

The treatment with the alkoxide or hydroxide typically occurs in an alcohol, such as methanol under reflux. The product obtained exhibits analytical purity.

The following non-limiting examples are presented to further illustrate the present invention, wherein all amounts are by weight, unless the contrary is stated, and all temperatures are normal room temperature, and pressures are normal atmospheric pressures, unless the contrary is stated.

To facilitate an understanding of the examples, the following chart is presented, identifying various example numbers and compound structure.

TABLE 1

Intermediates and Compound of the General Formula

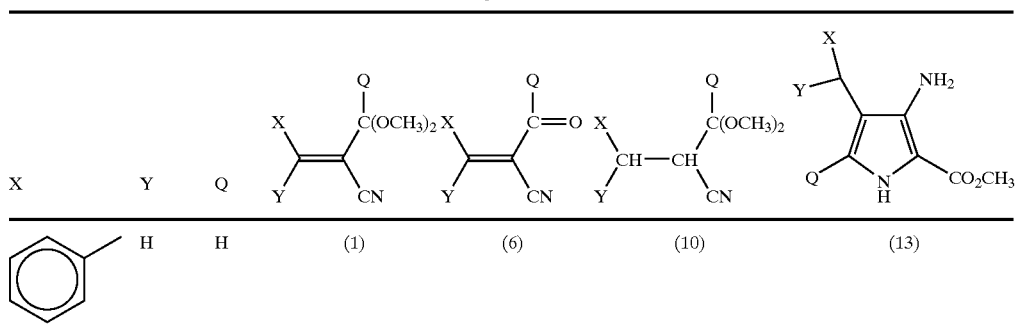

TABLE 1-continued

Intermediates and Compound of the General Formula

| X | | | | | | |
|---|---|---|---|---|---|---|
| 3-methylthiophene | H | H | (2) | (7) | — | (14) |
| tetrahydrothiopyran (S-cyclohexyl) | H | H | (3) | (8) | (11) | (15) |
| 3-pyridyl | H | H | (4) | — | (12) | (16) |
| 2-pyridyl | H | H | — | — | — | (17) |
| phenyl | H | CH$_3$ | (5) | (9) | — | (18) |
| 3-pyridyl | CH$_2$CN | H | — | — | — | (19) |

| X | pyrrole intermediate | pyrrolopyrimidine |
|---|---|---|
| phenyl | (R$_3$ = CH$_3$) (22) | 2B (31) |
| 3-methylthiophene | (R$_3$ = CH$_3$) (23) | 5B (32) |
| tetrahydrothiopyran | (R$_3$ = CH$_3$) (24) | 11C (33) |
| 3-pyridyl | (25) (R$_3$ = C(CH$_3$)$_3$) (R$_3$ = CH$_3$)(26) | (34) 34, 34D (35) |
| 2-pyridyl | — | 434 (36) |

TABLE 1-continued

Intermediates and Compound of the General Formula

| | | |
|---|---|---|
| 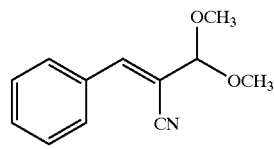 | (29) | 593 (37) |
| 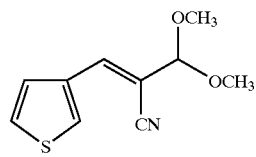 | — | 469 (38) |

EXAMPLE 1

Preparation of:

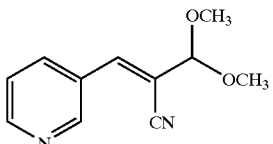

FW = 203.23

2-(Dimethoxymethyl)-3-phenylacrylonitrile

Benzaldehyde (79.5 g, 0.75 mol) and 3,3-dimethoxypropionitrile (115.1 g, 1.0 mol) were mixed together and added to a solution of sodium methoxide (54.0 g, 1.0 mol) in methanol (400 mL) over a period of 15 minutes. The mixture was stirred at room temperature overnight. Most of the methanol was evaporated in vacuo and the residue was partitioned between ethyl acetate (500 mL) and water (450 mL). The organic layer was separated, washed with brine (400 mL), dried (MgSO$_4$) and the solvent evaporated in vacuo. The residual oil was distilled to give 103 g (68%) of the product as a colorless oil, bp 125–130° C. (2 mm Hg).

Analysis: Calc. for $C_{12}H_{13}NO_2$: C, 70.92; H, 6.45; N, 6.89. Found: C, 70.68; H, 6.50; N, 6.88.

EXAMPLE 2

Preparation of:

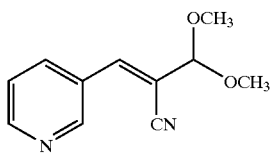

FW = 209.27

2-(Dimethoxymethyl)-3-(3-thienyl)acrylonitrile

Thiophene-3-carboxaldehyde (50.0 g, 0.45 mol) and 3,3-dimethoxypropionitrile (80.5, g, 0.7 mol) were mixed together and added to a solution of sodium methoxide (37.8 g, 0.7 mol) in methanol (250 mL) over a period of 15 minutes. The mixture was stirred at room temperature overnight. Most of the methanol was evaporated in vacuo and the residue was partitioned between ethyl acetate (500 mL) and water (450 mL). The organic layer was separated, washed with brine (400 mL), dried (MgSO$_4$) and the solvent evaporated in vacuo. The residual oil was distilled to give 65 g (69%) of the product as a colorless oil, bp 130–134° C. (2 mm Hg).

Analysis: Calc. for $C_{10}H_{11}NO_2$: C, 57.40; H, 5.30; N, 6.70. Found: C, 57.53; H, 5.40; N, 6.71.

EXAMPLE 3

Preparation of:

·0.25H$_2$O    FW = 209.29

2-(Dimethoxymethyl)-3-cyclohexylacrylonitrile

Cyclohexanecarboxaldehyde (50.0 g, 0.45 mol) was added to a stirred mixture of 3,3-dimethoxypropionitrile (11.5, g, 1.0 mol) and sodium methoxide (54.0 g, 1.0 mol) in methanol over a period of 15 minutes. The mixture was then stirred overnight at room temperature.

Most of the methanol was evaporated in vacuo and the residue was partitioned between ethyl acetate (600 mL) and brine (600 mL). The organic layer was separated, washed with brine (600 mL), dried (MgSO$_4$) and the ethyl acetate evaporated in vacuo. The residual oil was distilled in vacuo to give 23.2 g (25%) of the product as a pale-yellow oil, bp 125–30° C. (2 mm Hg).

Analysis: Calc. for $C_{12}H_{19}NO_2$: C, 68.87; H, 9.15; N, 6.69. Found: C, 68.43; H, 9.14; N, 6.92.

EXAMPLE 4

Preparation of:

FW = 204.23 (anhydrous)

·0.25H$_2$O

2-Dimethoxymethyl-3-(3-pyridyl)acrylonitrile hydrate (4:1)

Pyridine-3-carboxaldehyde (80.25 g, 0.75 mol) and 3,3-dimethoxypropionitrile (115.1 g, 1.0 mol) were mixed together and added to a solution of sodium methoxide (54.0 g, 1.0 mol) in methanol (400 mL) over a period of 15 minutes. The mixture was stirred at room temperature overnight. Most of the methanol was evaporated in vacuo and the residue was partitioned between ethyl acetate (500 mL) and water (450 mL). The organic layer was separated, washed with brine (400 mL), dried (MgSO$_4$) and the solvent evaporated in vacuo. The residual oil was distilled in vacuo to give 80.3 g (52%) of the product as a colorless oil, bp 130–140° C. (2 mm Hg).

Analysis: Calc. for $C_{11}H_{12}N_2O_2 \cdot 0.25H_2O$: C, 63.30; H, 6.04; N, 13.42. Found: C, 63.37; H, 6.03; N, 13.45.

EXAMPLE 5

Preparation of:

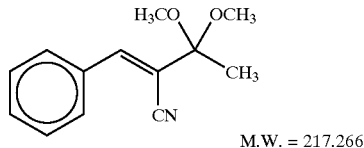

M.W. = 217.266

3-Cyano-4-phenyl-3-buten-2-one dimethylketal

A sample of 2,2-dimethoxyacetoacetonitrile[1] (15.0 g, 0.116 mol) and benzaldehyde (8.8 mL, 0.0872 mol) were mixed together in an additional funnel and added dropwise to a stirred solution of sodium methoxide (6.26 g, 0.116 mol) in methanol (60 mL). After the last addition, the mixture was allowed to stir overnight. The mixture was then concentrated to give a yellow residue which was partitioned between ethyl acetate (125 mL) and water (100 mL). The organic layer was separated, washed with brine (100 mL), and then dried over Na$_2$SO$_4$. The ethyl acetate was removed in vacuo and the residue subjected to vacuum distillation to remove unreacted benzaldehyde. This yielded 11.3 g (0.052 mol, 60%) of the crude product which was used without further purification. A portion of the material was triturated with cold hexane to give the product as colorless needles, mp 45–46° C.

[1] See U.S. Pat. No. 4,152,337 (1979) for method of preparation.

Analysis: Calc. for $C_{13}H_{15}NO_2$: C, 71.86; H, 6.95; N, 6.44. Found: C, 71.90; H, 6.91; N, 6.45.

EXAMPLE 6

Preparation of:

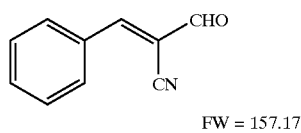

FW = 157.17

2-Cyano-3-phenylpropenal

A mixture of benzaldehyde (30.3 g, 0.3 mole) and 3,3-dimethoxypropionitrile (69.0 g, 0.06 mole) was added to a stirred mixture of sodium methoxide (32.4 g, 0.6 mole) in methanol (300 mL) over a period of 15 minutes. The mixture, which became warm during the addition, was stirred at room temperature for three days (for convenience). Most of the solvent was evaporated in vacuo and the residue was partitioned between water (450 mL) and ether (500 mL). The ether layer was separated, washed with water (400 mL), dried (MgSO$_4$) and evaporated in vacuo. The product was distilled in vacuo and the fraction boiling between 132–138° C. (2 mm Hg) was collected to give 51 g (84%) of the acetal as a colorless oil.

The above product (5.0 g 0.025 mole) and 6N hydrochloric acid (75 mL) were stirred together at room temperature for 30 minutes. The colorless solid was collected by filtration, washed with water and dried in air to give 3.9 g (100%). A portion was recrystallized from ether-hexane as colorless needles, mp 96–97° C.

Analysis: Calc. for $C_{10}H_7NO$: C, 76.42; H, 4.49; N, 8.91. Found: C, 76.17; H, 4.58; N, 8.83.

EXAMPLE 7

Preparation of:

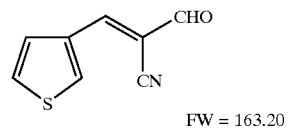

FW = 163.20

2-Cyano-3-(3-thienyl)propenal

The acetal, obtained from Example 2 (2.09 g, 0.01), was added to 6N HCl (50 mL) and the mixture was stirred at room temperature for one hour. The solid was collected by filtration, washed with water and dried in air to give 1.6 g (100%) of the aldehyde as a colorless solid. An analytical sample was recrystallized from ether as colorless needles, mp 123–4° C.

Analysis: Calc. for $C_5H_5NOS$: C, 58.88; H, 3.09; N, 8.59. Found: C, 58.92; H, 3.09; N, 8.58.

EXAMPLE 8

Preparation of:

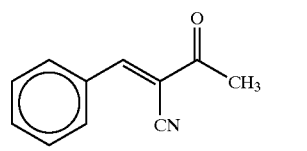

FW = 163.22

2-Cyano-3-cyclohexylpropenal 2-(Dimethoxymethyl)-3-cyclohexylacrylonitrile, obtained from Example 3 (4.18 g, 0.02 mol) and 6N HCl (50 mL) were stirred together overnight at room temperature. The product was extracted with ethyl acetate (200 mL), the extract was dried) (MgSO$_4$) and the ethyl acetate was evaporated in vacuo to give a 2.5 g (76%) of a brown oil which was used directly. A sample was distilled in a kugelrohr apparatus to give a pale yellow oil from which an analytical 2,4-dinitrophenyl hydrazone derivative was obtained as orange needles, mp 228–30° C.

Analysis: Calc. for $C_{16}H_{17}N_5O_4$: C, 55.97; H, 4.99; N, 20.40. Found: C, 55.76; H, 4.98; N, 20.30.

EXAMPLE 9

Preparation of:

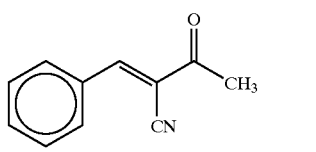

M.W. = 171.198

2-Cyano-4-phenyl-3-buten-2-one

A sample of 3-cyano-4-phenyl-3-buten-2-one dimethylketal, prepared in accordance with the procedure of Example 5 (5.0 g, 23 mmol) was suspended in 6N HCl (100 mL) and stirred at room temperature for 72 h[1]. Thin layer chromatographic analysis (SiO$_2$, hexane—ethyl acetate 7:3) indicated nearly complete conversion of the ketal to the lower R$_f$ ketone which had deposited along the bottom of the reaction flask as a yellow solid. The solid was purified by column chromatography (SiO$_2$, hexane—ethyl acetate 9:1) and the desired fractions evaporated to give 1.5 g (38%) of 3-cyano-4-phenyl-3-buten-2-one, as colorless needles, mp 83–84° C. (lit. 80–81° C.[2]).

[1] It was found that filtering the solid after 2 h and using fresh 6N HCl completed the hydrolysis easily in one day.
[2] See J. Org. Chem., 53(10), 2238–45 (1988) for an alternative preparation. See also Tetrahedron, 49(23), 5091–8 (1993); Tetrahedron Lett. 28(9), 913–16 (1987); J. Chem. Soc., Perkin Trans. 1, 12, 2581–4 (1985); Heterocycles, 23(12), 2983–8 (1984); Heterocycles, 22(9), 1989–93 (1984); J. Heterocyl. Chem., 19(5), 1073–6 (1982) for other preparations.

Analysis: Calc. for C$_{11}$H$_9$NO: C, 77.17; H, 5.29; N, 8.18. Found: C, 77.15; H, 5.35; N, 8.18.

EXAMPLE 10

Preparation of:

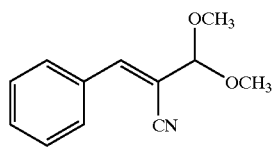

FW = 205.25

2-Cyano-3-phenylpropionaldehyde dimethylacetal

The acetal, obtained from Example 1 (40.6 g, 0.2 mol), was dissolved in methanol (300 mL) and 10% palladium on carbon (1 g) was added. The mixture was shaken in a 500 mL Parr reactor under ca 50 psig hydrogen pressure overnight. The catalyst was removed by filtration and the solvent was evaporated in vacuo. The residual oil was distilled to give 30.2 g (74%) of the product as a colorless oil, bp 133–135° C. (2 mm Hg).

Analysis: Calc. for C$_{12}$H$_{15}$NO$_2$: C, 70.22; H, 7.37; N, 6.82. Found: C, 70.30; H, 7.32; N, 6.89.

EXAMPLE 11

Preparation of:

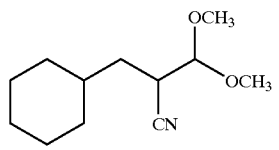

FW = 211.31

2-Cyano-3-cyclohexylpropionaldehyde dimethylacetal

3-Cyclohexyl-2-dimethoxymethylacrylonitrile, obtained from Example 3 (8.3 g, 0.04 mol), methanol (100 mL) and 10% palladium on carbon (0.3 g) were shaken together in a Parr bottle under 50 psig hydrogen pressure for 30 minutes. The catalyst was removed by filtration and the methanol was evaporated in vacuo to give the product as a pale-yellow oil (8.3 g, 100%).

Analysis: Calc. for C$_{12}$H$_{21}$NO$_2$: C, 68.21; H, 10.02; N, 6.63. Found: C, 68.38; H, 9.75; N, 6.71.

EXAMPLE 12

Preparation of:

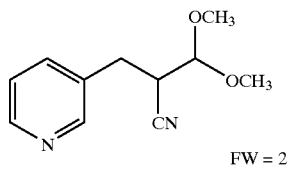

FW = 206.25

2-Cyano-3-(3-pyridyl)propionaldehyde dimethylacetal

A mixture of 2-dimethoxymethyl-3-(3-pyridyl)acrylonitrile, obtained according to the process of Example 4 (20.4 6, 0.1 mol), absolute ethanol (200 mL) and sodium borohydride (1.6 g, 0.042 mol) was stirred at room temperature overnight. Most of the ethanol was evaporated in vacuo and the residue was partitioned between ethyl acetate (200 mL) and water (200 mL). The organic layer was separated, washed with saturated brine, dried (Na$_2$SO$_4$) and evaporated in vacuo. The residual oil was distilled in vacuo to give a pale-yellow oil (19.1 g, 93%), bp. 130–140° C. (0.2 mm Hg).

Analysis: Calc. for C$_{11}$H$_{14}$N$_2$O$_2$: C, 64.06; H, 6.84; N, 13.58. Found: C, 63.90; H, 6.81; N, 13.66.

EXAMPLE 13

Preparation of:

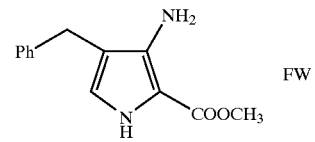

FW = 230.27

Methyl 3-Amino-4-Phenylmethyl-1H-Pyrrole-2-Carboxylate

2-Cyano-3-phenylpropenal, obtained from Example 6 (3.14 g, 0.02 mol), methanol and 10% palladium on carbon (0.2 g) were shaken together under ca 50 psig hydrogen in a 500 mL Parr hydrogenation bottle until hydrogen uptake ceased (ca 35 min.). The catalyst was removed by filtration and a mixture of diethyl aminomalonate hydrochloride (6.35 g, 0.03 mol), sodium acetate (2.46 g, 0.03 mol) and water (20 mL) was added. The mixture was stirred at room temperature overnight.

Most of the solvent was evaporated in vacuo and the residue was partitioned between ethyl acetate (250 mL) and water (200 mL). The organic layer was separated, dried (MgSO$_4$) and evaporated in vacuo. The residual yellow oil was dissolved in methanol (100 mL) containing sodium methoxide (0.54 g, 0.01 mol) and the mixture was stirred at room temperature for 2 hours. Most of the methanol was evaporated in vacuo and the residue was triturated with water to give the product as a light-yellow solid (1.3 g, 57%). An analytical sample was crystallized from cyclohexane as light-yellow needles, mp 98–100° C. (lit[1] 96–98° C.).

[1] Montgomery, J. A.; Niwas, S.; Rose, J. D.; Secrist, J. A., III, Babu, Y. S.; Bugg, C. E.; Erion, M. D.; Guida, W. C.; Ealick, S. E., J. Med. Chem., 1993, 58–55.

Analysis: Calc. for C$_{13}$H$_{14}$N$_2$O$_2$: C, 67.81; H, 6.13; N, 12.16. Found: C, 67.82; H, 6.16; N, 12.16.

EXAMPLE 14

Preparation of:

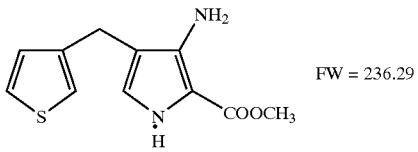

FW = 236.29

Methyl 3-Amino-4-(3-Thienylmethyl)-1H-Pyrrole-2-Carboxylate

The aldehyde, obtained from Example 7 (1.63 g, 0.01 mol), methanol (100 mL) and 10% palladium on carbon (0.3 g) were shaken together under ca 50 psig hydrogen pressure in a 500 mL Parr reactor for one hour. The catalyst was removed by filtration, diethyl aminomalonate hydrochloride (2.3 g, 0.011 mol), sodium acetate (1.0 g, 0.012 mol) and water (20 mL) were added and the mixture was stirred at room temperature overnight. Most of the methanol was evaporated in vacuo and the mixture partitioned between ethyl acetate (200 mL) and water (200 mL). The organic layer was separated, dried (MgSO$_4$) and evaporated in vacuo. The residual yellow oil was dissolved in methanol (50 mL) containing sodium methoxide (0.54 g, 0.01 mol) and the mixture was stirred at room temperature for 2 hours. Most of the methanol was evaporated in vacuo and the residue was treated with water (200 mL). The oil solidified on standing and the product was recrystallized from toluene-cyclohexane (1:3) to give the pyrrole as colorless needles, mp 108–110° C. (lit[1] 108–109° C.), 0.8 g (34%).

[1] Montgomery, J. A.; Niwas, S.; Rose, J. D.; Secrist, J. A., III, Babu, Y. S.; Bugg, C. E.; Erion, M. D.; Guida, W. C.; Ealick, S. E., J. Med. Chem., 1993, 58–55.

Analysis: Calc. for $C_{11}H_{12}N_2O_2$: C, 55.91; H, 5.12; N, 11.85. Found: C, 55.84; H, 5.20; N, 11.75.

EXAMPLE 15

Preparation of:

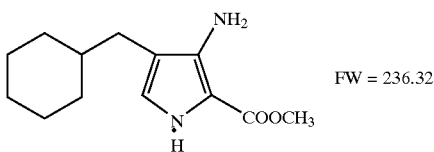

FW = 236.32

Methyl 3-amino-4-(cyclohexylmethyl)-1H-pyrrole-2-carboxylate

2-Cyano-3-(cyclohexyl)propenal, obtained from Example 8 (24.5 g, 0.15 mol), methanol (300 mL) and 10% palladium on carbon (0.7 g) were shaken together under 60 psig hydrogen pressure until uptake ceased (ca one hour). The catalyst was removed by filtration, diethyl aminomalonate hydrochloride (42.2 g, 0.2 mol), sodium acetate (16.4 g, 0.2 mol) and water (100 mL) were added and the mixture was stirred at room temperature overnight.

Most of the methanol was evaporated in vacuo and the residue was partitioned between water (500 mL) and ethyl acetate (400 mL). The organic layer was separated, washed with water (400 mL), dried (MgSO$_4$) and the ethyl acetate removed in vacuo to give 34.0 g of a pale yellow oil. The oil was dissolved in methanol (500 mL) containing sodium methoxide (10.8 g, 0.2 mol) and the mixture was stirred at room temperature for 4 hours.

Most of the methanol was evaporated in vacuo and the residue was treated with water (500 mL) containing acetic acid (2 mL). The oil was extracted with ethyl acetate (400 mL), the extract dried (MgSO$_4$) and the ethyl acetate was evaporated in vacuo to give the product (20.1 g, 56%) as a yellow oil which solidified on trituration with petroleum ether to give a white solid, mp 79–80° C. (lit[1] 73–4° C.).

[1] Secrist, J. A., III; Niwas, S.; Rose, J. D.; Babu, Y. S.; Bugg, C. E.; Erion, M. D.; Guida, W. C.; Ealick, S. E.; Montgomery, J. A.; J. Med. Chem., 1993, 36, 1847.

Analysis: Calc. for $C_{13}H_{20}N_2O_2$: C, 66.07; H, 8.53; N, 11.85. Found: C, 66.18; H, 8.61; N, 11.86.

EXAMPLE 16

Preparation of:

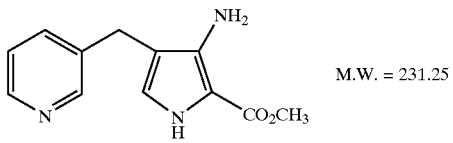

M.W. = 231.25

Methyl 3-Amino-4-(3-Pyridylmethyl)-1H-Pyrrole-2-Carboxylate 3-(3-pyridyl)propionitrile (77.5 g, 0.59 mol) was added slowly during 10 min to a mechanically stirred suspension of sodium hydride (21 g, 0.875 mol; 60% dispersion in mineral oil) in THF (1 L). Ethyl formate (15 mL) was added to initiate the reaction and vigorous gas evolution was observed after 10 min. The mixture was cooled with ice water and a further 100 mL of ethyl formate was added dropwise during a period of 6 h to control the gas evolution. The mixture was than stirred at room temperature overnight.

During the second day, additional amount of sodium hydride (35.35 g, 0.384 mol) was added in 3 equal portions at 3 h intervals while ethyl formate (175 mL) was added dropwise during 8 h. The mixture was again stirred overnight at room temperature.

During the third day, completion of the reaction was confirmed by tlc (CHCl$_3$/CH$_3$CH, 93/7; Rf 0.25 with positive Rosaniline test). The sodium salt of the desired formyl compound was filtered off, washed with 600 mL of hexane (to remove any remaining oil introduced with the sodium hydride) and partially dried under nitrogen (CAUTION: any remaining sodium hydride may cause the product to spontaneously ignite in air, especially if the material is completely dried). The salt, which was off-white in color, was used as is in the next step without further purification and with an assumed quantitative yield of 106.8 g.

The crude 2 cyano-3-(3-pyridyl)propionaldehyde sodium enolate obtained above (106.81 g, 0.586 mol) was added cautiously to a mechanically stirred mixture of methanol (800 mL) and water (300 mL) with ice water cooling. Diethyl aminomalonate hydrochloride (137.2 g, 0.546 mol) was added and after 5 min all the reactants had dissolved. The pH was adjusted to about 5.5 with careful addition of 6N HCl and the mixture was stirred at room temperature for 48 h. The progress of the reaction was monitored by tlc using CHCl$_3$/CH$_3$OH (93:7), the product having Rf of 0.35 was a mixture of cis-trans isomers. The methanol was evaporated in vacuo, the product was extracted into ethyl acetate (1×600 mL and 1×300 mL), the combined extracts were washed with water (600 mL) containing saturated brine solution (100 mL). The dried (Na$_2$SO$_4$) extract was evaporated under reduced pressure below 30° C. and dried in vacuo to yield 177.3 g (95.3%) of crude diethyl (2-cyano-2-(3-pyridyl) methyl)-vinyl)aminomalonate as a thick yellow oil.

The crude enamine obtained above (176.5 g, 0.556 mol) was dissolved in the methanol (1 L) and stirred with ice-bath cooling while 25 wt. % sodium methoxide solution in methanol (146.4 mL, 0.64 mol) was added. The mixture became dark brown and was stirred at room temperature for 3 days. The methanol was evaporated in vacuo and water, (500 mL) was added. The procedure was filtered off, washed with water (2×200 mL) and dried in air to yield 90 g (66% overall; 3 steps from starting propionitrile) as an off-white solid, mp 136–138° C. (lit[1] mp 135–136° C.).

[1] John A. Montgomery, Shri Niwas, Jerry D. Rose, John A. Secrist, Y. S. Babu, Charles E. Bugg, Mark D. Erion, Wayne C. Guida, and Steven E. Ealick J. Med. Chem. 36, 55–69 (1993).

Analysis: Calc. for $C_{12}H_{13}N_3O_2$: C, 62.23; H, 5.67; N, 18.17. Found: C, 62.30; H, 5.70; N, 18.11.

EXAMPLE 17
Preparation of:

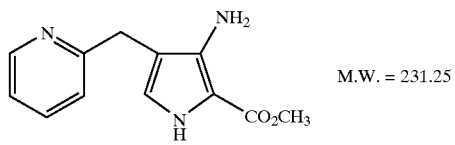

M.W. = 231.25

Methyl 3-Amino-4-(2-pyridylmethyl)-1H-pyrrole-2-carboxylate 3-(2-pyridyl)propionitrile (12.75 g, 96.44 mmol) was added slowly during 10 min to a mechanically stirred suspension of sodium hydride (3.48 g, 144.94 mmol; 60% dispersion in mineral oil) in THF (165 mL). Ethyl formate (2 mL) was added to initiate the reaction and vigorous gas evolution was observed during first 10 min. The mixture was cooled with ice water and a further 25 mL of ethyl formate was added dropwise during a period of 3 h to control the gas evolution. The mixture was then stirred at room temperature overnight.

During the second day, additional amount of sodium hydride (3.48 g, 144.94 mmol) was added in 3 equal portions at 3 h intervals while ethyl formate (25 mL) was added dropwise during 6 h. The mixture was again stirred overnight at room temperature.

During the third day, completion of the reaction was confirmed by tlc ($CHCl_3/CH_3CH$, 93/7; Rf 0.3 with positive Rosaniline test). The sodium salt of the desired formyl compound was filtered off, washed with 20 mL of hexane (to remove any remaining oil introduced with the sodium hydride) and partially dried under nitrogen. The salt which was off-white in color, was used as is in the next step without further purification and with an assumed quantitative yield of 17.57 g.

The crude 2-cyano-3-(2-pyridyl)propionaldehyde sodium enolate obtained above (17.57 g, 96.44 mmol) was added to a stirred mixture of methanol (150 mL) and water (80 mL) with ice water cooling. Diethyl aminomalonate hydrochloride (24.02 g, 113.5 mmol) was added and after 5 min all the reactants had dissolved. The pH was adjusted to about 6.5 with 6N HCl and the mixture was stirred at room temperature for 15 h. The progress of the reaction was monitored by tlc using $CHCl_3/CH_3OH$ (93:7), the product having Rf of 0.4 was a mixture of cis-trans isomers. The methanol was evaporated in vacuo, the product was extracted into ethyl acetate (300 mL), and the extract was washed with water (200 mL) containing saturated brine solution (50 mL). The dried ($Na_2SO_4$) extract was evaporated under reduced pressure below 30° C. and dried in vacuo to yield 16.0 g (52.3%) of crude diethyl (2-cyano-2-(2-pyridyl)methyl)-vinyl) aminomalonate as a thick, yellow oil.

The crude enamine obtained above (16.0 g, 50.4 mol) was dissolved in the methanol (100 mL) and stirred with ice-bath cooling while 25 wt. % sodium methoxide solution in methanol (12.7 mL 55.47 mmol) was added. The mixture became dark brown and was stirred at room temperature for 2 days. The methanol was evaporated in vacuo, and the residue was extracted into ethyl acetate, washed with water dried over sodium sulfate and evaporated in vacuo to give a brown residue (8.0 g). This residue was chromatographed (Silica gel: $MeOH:CHCl_3$, 3:97) to afford 2.6 g (11.7% overall; 3 steps from starting propionitrile) of methyl-3-amino-4-[(2-pyridyl)methyl]-1H-pyrrole-2-carboxylate.

Analysis: Calc for $C_{12}H_{13}N_3O_2$: C, 62.23; H, 5.67; N, 18.17. Found: C, 62.39; H, 5.71; N, 18.10.

EXAMPLE 18
Preparation of:

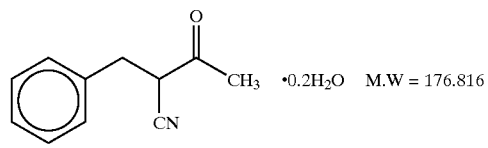

·$0.2H_2O$  M.W = 176.816

3-Cyano-4-phenylbutane-2-one hydrate (5:1)[1]

A sample of 3-cyano-4-phenyl-3-buten-2-one, prepared according to the procedure of Example 9 (5.0 g, 29.24 mmol), was dissolved in methanol (100 mL) containing 10% Pd—C (ca. 0.1 g, Aldrich) and hydrogenated at 50 psi hydrogen pressure for 2 h. The mixture was filtered through Celite to remove catalyst and an analytical sample prepared by concentrating a portion of the filtrate to give a pale-yellow oil. The oil was passed through a short pad of silica gel (hexane—ethyl acetate 7:3) and the desired fractions evaporated to give the title compound as a straw-colored oil. The remaining material was used directly in the next step.

[1] This material should be kept at 0° C., as it appears to decompose at room temperature over a short period of time.

Analysis: Calc. for $C_{11}H_{11}NO$-$0.2H_2O$: C, 74.72; H, 6.49; N, 7.92. Found: C, 74.76; H, 6.39; N, 7.58.

EXAMPLE 19
Preparation of

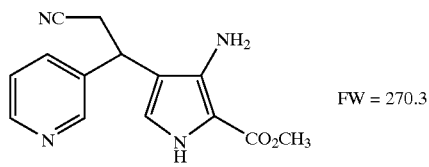

FW = 270.3

Methyl 3-Amino-4-[2-cyano-1-(3-pyridyl)ethyl]-1H-pyrrole-2-carboxylate 3-(3-pyridyl)pentanedinitrile (12 g, 58.41 mmol), obtained as a brown solid, mp 60–64° C., by a reported procedure for a similar series of compounds,[1] was added to a mechanically stirred suspension of sodium hydride (2.1 g 87.5 mmol; 60% dispersion in mineral oil) in THF (100 mL).

Ethyl formate (2 mL) was added to initiate the reaction and then 18 mL was added dropwise during a period of 1.5 h to control the gas evolution. The mixture was then stirred at room temperature overnight.

[1] Mark D. Erion, S. Niwas, Jerry D. Rose, S. Ananthan, Mark Allen, John A. Secrist III, Y. Sudhakar Babu, Charles E. Bugg, Wayne C. Guida, Steven E. Ealick, and John A. Montgomery J. Med. Chem. 1993, 36, 3771–83.

During the second day, completion of the reaction was confirmed by tlc (CHCl$_3$/CH$_3$OH, 93/7; Rf 0.25 with positive Rosaniline test). The solvent was evaporated in vacuo, and the residue was washed with hexane (3×50 mL) to remove oil introduced with the sodium hydride. The brown residue was then used as is in the next step without further purification and with an assumed quantitative yield of 12.92 g.

The crude 2-cyano-3-cyanomethyl-3-(3-pyridyl)propionaldehyde sodium enolate obtained above (12.9 g, 58.41 mmol) was added to a stirred mixture of methanol (100 mL) and water (85 mL) with ice-water cooling. Diethyl aminomalonate hydrochloride (13.59 g, 64.25 mmol) was added and after 5 min all the reactants had dissolved. The pH was adjusted to about 6.5 with 6N HCl and the mixture was stirred at room temperature for 20 h. The progress of the reaction was monitored by tlc using CHCl$_3$/CH$_3$CH (93:7), the product having Rf of 0.4 was a mixture of cis-trans isomers. The methanol was evaporated in vacuo, the product was extracted into ethyl acetate (220 mL) and washed with water (200 mL). The dried (Na$_2$SO$_4$) extract was evaporated under reduced pressure below 30° C. and dried in vacuo to yield 20.2 g (97%) of crude diethyl N-(2-cyano-2-[1-(3-pyridyl)-2-cyanoethyl])-vinylaminomalonate as a thick, yellow oil.

The crude enamine obtained above (20.2 g, 56.68 mmol) was dissolved in methanol (200 mL) and stirred with ice-bath cooling while 25 wt. % sodium methoxide solution in methanol (13.44 mL, 62.35 mol) was added. The mixture became dark brown and was stirred at room temperature for 20 h. Additional sodium methoxide (3.35 g, 56.68 mmol, 13.44 mL of 25 wt. % solution) was added and the reaction mixture was heated at reflux overnight. The methanol was evaporated in vacuo and water (250 mL) was added. The product was isolated by filtration, washed with water (2×50 mL), hexane (25 mL), and crystallized from hot ethyl acetate to yield 6.31 g of the desired pyrrole (40% overall; 3 steps from starting dinitrile) as an off-white solid, mp 179–180° C.

Analysis: Calc for C$_{14}$H$_{14}$N$_4$O$_2$: C, 62.21; H, 5.22; N, 20.73. Found: C, 62.27; H, 5.25; N, 20.69.

EXAMPLE 20

Preparation of:

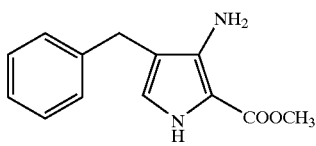

3-amino-2-methoxycarbonyl-4-[(phenyl)methyl]-H-pyrrole

2-Cyano-3-phenylpropionaldehyde dimethylacetal, obtained according to the method of Example 10 (3.1 g), is added to 6N hydrochloric acid (20 mL) and the mixture is stirred overnight at room temperature. The product is extracted into ethyl acetate (200 mL) and the ethyl acetate is evaporated in vacuo. The residue is dissolved in methanol (50 mL) containing water (20 mL) and diethyl aminomalonate hydrochloride (4.2 g) and sodium acetate (1.7 g) are added. The mixture is then stirred at room temperature overnight. Most of the methanol is evaporated in vacuo and the residue is partitioned between ethyl acetate (100 mL) and water (100 mL). The organic layer is dried (MgSO$_4$) and the ethyl acetate is evaporated in vacuo. The residue is dissolved in methanol (75 mL) containing sodium methoxide (1.1 g) and the mixture is stirred at room temperature for three hours. Most of the methanol is evaporated in vacuo and the residue is treated with water to precipitate the product which is purified by crystallization from methanol.

EXAMPLE 21

Preparation of:

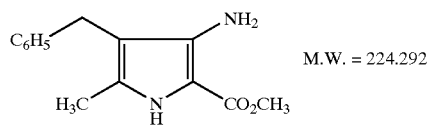

M.W. = 224.292

Methyl 3-amino-5-methyl-4-(phenylmethyl)-1H-pyrrole-2-carboxylate

A sample of 3-cyano-4-phenylbutane-2-one-hydrate, obtained from Example 18 (5.0 g, 29.24 mmol), was dissolved in methanol (100 mL) to which was added water (2 mL) sodium acetate (3.55 g, 43.35 mmol) and diethylaminomalonate hydrochloride (9.17 g, 43.35 mmol), and the mixture allowed to stir overnight. The mixture was concentrated and the residue partitioned between ethyl acetate (200 mL) and water (150 mL). The organic layer was separated and dried thoroughly over MgSO$_4$. The mixture was filtered and the filtrate concentrated to give the crude enamine as a semi-crystalline material which was used without further purification.

The enamine was dissolved in absolute methanol (100 mL) to which was added sodium methoxide (1.56 g, 28.90 mmol) in one-portion. The mixture was stirred for 2 h at ambient temperature and then concentrated in vacuo. The residue was partitioned between ethyl acetate (200 mL) and water (150 mL) and the organic layer was separated, dried (Na$_2$SO$_4$) and concentrated to give a viscous orange mass consisting of the mixed methyl and ethyl 3-amino-5-methyl-4-(phenylmethyl)pyrrole-2-carboxylates.

A portion of mixed methyl and ethyl 3-amino-5-methyl-4-(phenylmethyl)pyrrole-2-carboxylate was dissolved in absolute methanol containing an excess of sodium methoxide solution (25% solution in methanol, Aldrich). The mixture was heated at reflux overnight and then cooled to ambient temperature. The mixture was concentrated and the residue partitioned between ethyl acetate and water. The ethyl acetate layer was separated and dried over sodium sulfate. The solution was filtered and concentrated to give a residue which was purified by column chromatography (SiO$_2$, hexane—ethyl acetate 7:3). An analytical sample was prepared by recrystallization from isopropyl alcohol to give methyl 3-amino-5-methyl-4-(phenylmethyl)pyrrole-2-carboxylate, as pale-yellow crystals, mp 143–144° C.

Analysis: Calc. for C$_{14}$H$_{16}$N$_2$O$_2$: C, 68.83; H, 6.60; N, 11.46. Found: C, 68.91; H, 6.65; N, 11.45.

EXAMPLE 22

Preparation of:

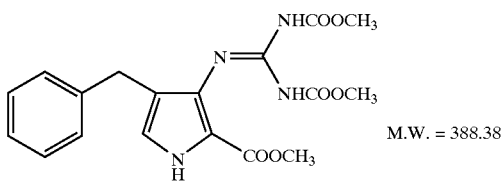

M.W. = 388.38

Methyl 3-(N,N'-bis-carbomethoxyguanidinyl)-4-(phenylmethyl)-1H-pyrrole-2-carboxylate Methyl 3-amino-4-(phenylmethyl-1H-pyrrole-2-carboxylate, obtained from Example 13 (0.4 g, 1.7 mmol), was dissolved in acetonitrile (10 mL) followed by triethylamine (0.53 g, 0.72 mL, 5.2 mmol), 3 eq) and 1,3-dicarbomethoxy-2-methyl-2-thiopseudourea, obtained according to the procedure of Example 27 (0.4 g, 1.9 mmol, 1.1 eq). The solution was stirred for 10 minutes at room temperature and mercuric chloride (0.6 g, 2.2 mmol, 1.3 eq) was added. A precipitate appeared almost immediately. The slurry was allowed to continue stirring for 65 hours (for convenience) at room temperature. The volatiles were removed in vacuo and the resulting paste stirred in water for 30 minutes. The solids were collected by filtration and extracted with boiling methanol (50 mL). The methanol extract was concentrated in vacuo and the resulting solid recrystallized from 2-propanol to give the title compound (0.111 g, 0.3 mmol, 17% yield) as a white solid, mp 158–160° C.

Analysis: Calc. for $C_{18}H_{20}N_4O_6$: C, 55.67; H, 5.19; N, 14.43. Found: C, 55.40; H, 5.22; N, 14.32.

EXAMPLE 23

Preparation of:

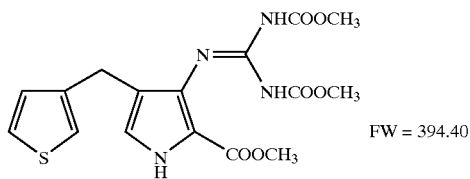

FW = 394.40

Methyl 3-(N,N'-bis-carbomethoxyguanidinyl)-4-(3-thienylmethyl)-1H-pyrrole-2-carboxylate Methyl 3-amino-4-(3-thienylmethyl)-1H-pyrrole-2-carboxylate, obtained from Example 14 (11.8 g, 0.05 mol), N,N'-bis-carbomethoxy-S-methylisothiourea (11.3 g, 0.055 mol) and triethylamine were stirred together in dimethyl formamide (100 mL) and cooled to 5° C. Mercuric chloride (14.9 g, 0.055 mol) was added and an immediate precipitate was observed. The mixture was stirred at room temperature overnight.

The solvent was evaporated in vacuo, the solid residue washed with water (400 mL) and extracted with hot methanol (400 mL). The methanol was evaporated in vacuo and the residue crystallized from toluene to give 12.9 g (66%) of product as colorless needles, mp 168–70° C.

Analysis: Calc. for $C_{16}H_{18}N_4O_6S$: C, 48.73; H, 4.60; N, 14.21. Found: C, 48.71; H, 4.73; N, 14.25.

EXAMPLE 24

Preparation of:

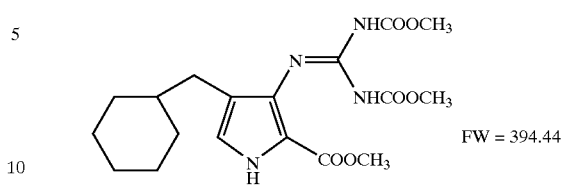

FW = 394.44

Methyl 3-(N,N'-bis-carbomethoxyguanidinyl)-4-(cyclohexylmethyl)-1H-pyrrole-2-carboxylate The pyrrole, obtained from Example 15 (4.72 g, 0.02 mol), N,N'-bis-carbomethoxy-S-methylisothiourea (4.54 g, 0.022 mol) and triethylamine (7.2 g, 0.07 mol) were stirred together at room temperature in acetonitrile (100 mL) and mercuric chloride (5.96 g, 0.022 mol) was added. There was an immediate precipitate and the mixture was stirred overnight.

The solvent was evaporated in vacuo, and the residue was extracted with boiling methanol (200 mL). The hot solution was filtered and the methanol was evaporated in vacuo. The residue was crystallized from 2-propanol as colorless needles, mp 171–2° C. (4.7 g, 60%).

Analysis: Calc. for $C_{18}H_{26}N_4O_6$: C, 54.81; H, 6.64; N, 14.20. Found: C, 54.55; H, 6.67; N, 14.07.

EXAMPLE 25

Preparation of:

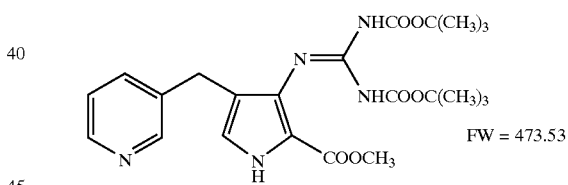

FW = 473.53

Methyl 3-[(N,N'-di(tert-butoxycarbobyl)guanidinyl]-4-(3-pyridylmethyl)-1H-pyrrole-2-carboxylate The pyrrole, obtained from Example 16 (1.16 g, 0.005 mol), N,N'-di(tert-butoxycarbonyl)thiourea (1.47 g, 0.0055 mol), triethylamine (1.8 g, 0.0175 mol) and DMF (25 mL) were stirred together at 4° C. and mercuric chloride (1.5 g, 0.0055 mol) was added. The mixture was then stirred at room temperature overnight. Most of the solvent was evaporated in vacuo, and the residue was treated with water to precipitate a brown solid which was collected by filtration, washed with water and dried in air. The solid was extracted with hot methanol (100 mL), and the methanol was evaporated in vacuo to give 1.8 g (76%) of product as an off-white solid. An analytical sample was recrystallized from chloroform-hexane as colorless prisms, mp 228–232° C.

Analysis: Calc. for $C_{23}H_{31}N_5O_6$: C, 58.34; H, 6.60; N, 14.79. Found: C, 58.16; H, 6.63; N, 14.59.

EXAMPLE 26

Preparation of:

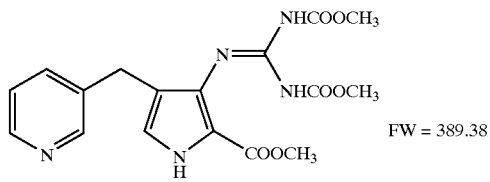

FW = 389.38

Methyl 3-(N,N'-bis-carbomethoxyguanidinyl)-4-(3-pyridylmethyl)-1H-pyrrole-2-carboxylate Methyl 3-amino-4-(3-pyridylmethyl)-1H-pyrrole-2-carboxylate, obtained from Example 16 (2.31 g, 0.01 mol), N,N'-bis-carbomethoxy-S-methylisothiourea (2.27 g, 0.011 mol) and triethylamine (3.6 g, 0.35 mol) were stirred together in acetonitrile (50 mL) and cooled to 5° C. Mercuric chloride (2.98 g, 0.011 mol) was added and an immediate precipitate was observed. The mixture was stirred at room temperature overnight.

The solvent was evaporated in vacuo, the solid residue washed with water (100 mL) and extracted with hot methanol (200 mL). The methanol was evaporated in vacuo and the residue crystallized from benzene-hexane to give 3.8 g (74%) of product as off-white needles, mp 166–8° C.

Analysis: Calc. for $C_{17}H_{19}N_5O_6$: C, 52.44; H, 4.92; N, 17.99. Found: C, 52.50; H, 5.00; N, 17.55.

EXAMPLE 27

Preparation of:

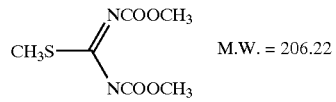

M.W. = 206.22

1,3-Dicarbomethoxy-2-methyl-2-thiopseudourea

2-Methyl-2-thiopseudourea sulfate (38.5 g; 138 mmol; 1 eq) was suspended in 150 mL of water and cooled to 0–5° C. Methyl chloroformate (56.6 g, 599 mmol; 4.3 eq) was added and the mixture was stirred for 5 minutes. Sodium hydroxide solution (25% w/w) was added drop-wise until the pH reached 9 (by pH paper). The white solid was collected by filtration and air dried to give 1,3-dicarbomethoxy-2-methyl-2-thiopseudourea (40.0 g, 70%) as a white solid, mp 99–101° C. An analytical sample, mp 100–102° C., was obtained by sublimation.

Analysis: Calc. for $C_6H_{10}N_2O_4S$: C, 34.95; H, 4.89; N, 13.58. Found: C, 34.88; H, 4.88; N, 13.62.

EXAMPLE 28

Preparation of:

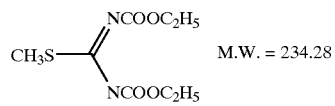

M.W. = 234.28

1,3-Dicarboethoxy-2-methyl-2-thiopseudourea

2-Methyl-2-thiopseudourea sulfate (15 g; 53.9 mmol; 1 eq) was suspended in 20 mL of water and cooled to 0–5° C. Ethyl chloroformate (29.2 g, 269 mmol; 5 eq) was added and the mixture was stirred for 5 minutes. Sodium hydroxide solution (25% w/w) was added drop-wise until the pH reached 8 (by pH paper). The white solid was collected by filtration and air dried to give 1,3-dicarboethoxy-2-methyl-2-thiopseudourea (22.2 g, 88%) as a white solid, mp 42–44° C. A small portion was dried in vacuo for analysis.

Analysis: Calc. for $C_8H_{14}N_2O_4S$: C, 41.01; H, 6.02; N, 11.96. Found: C, 41.09; H, 6.00; N, 11.89.

EXAMPLE 29

Preparation of:

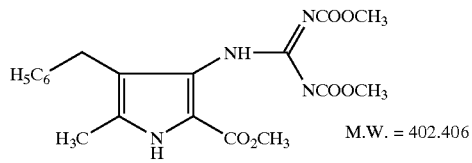

M.W. = 402.406

Methyl 3{[methoxycarbonylamino)methoxycarbonylimino]methyl} amino-5-methyl-4-phenylmethylpyrrole-2-carboxylate A sample of methyl 3-amino-5-methyl-4-phenylmethylpyrrole-2-carboxylate, obtained from Example 21 (0.46 g, 0.00189 mol) was suspended in methanol (3.80 mL) and acetic acid (0.54 mL, 0.00943 mol). 1,3-Dicarbomethoxy-2-methyl-2-thiopseudourea, obtained by the process according to Example 27 (0.427 g, 0.00207 mol), was added to this mixture. After 2.5 h the mixture became homogenous and in 22 h, thin layer chromatographic analysis ($SiO_2$, 7:3 hexane/ethyl acetate) indicated formation of a new, lower-running spot ($R_f$=0.0). The precipitate was removed by filtration and dried in vacuo at acetone reflux to give 0.544 g (72%) of a white solid which was recrystallized from isopropyl alcohol. The solid was dried in vacuo at acetone reflux to give the subject compound, as a white solid, mp 162.8–165.8° C.

Analysis: Calc. for $C_{19}H_{22}N_4O_6$: C, 56.72; H, 5.47; N, 13.93. Found: C, 56.97; H, 5.54; N, 13.91.

EXAMPLE 30

Preparation of:

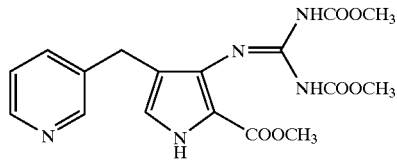

Methyl 3-(N,N'-bis-carbomethoxyguanidinyl)-4-(3-pyridylmethyl)-1H-pyrrole-2-carboxylate N,N'-bis-carbomethoxy-S-methylisothiourea (3.09 g, 0.015 mol) and methylene chloride (50 mL) were stirred together at room temperature and sulfuryl chloride (6.0 g, 0.045 mol) was added. The mixture was stirred for a further 3 hours and the solvent was evaporated in vacuo. Acetonitrile (100 mL) was added to dissolve the residue and methyl 3-amino-4-(3-pyridylmethyl)-1H-pyrrole-2-carboxylate, obtained from Example 16 (2.0 g, 0.0087 mol), was added to the stirred solution. After 2 hours, the solvent was evaporated in vacuo and the residue was dissolved in water (100 mL). The solution was made basic with solid sodium bicarbonate and the solid was collected by filtration, washed with water and dried in air. Crystallization from 2-propanol gave the product (1.2 g, 35%) as off-white needles.

EXAMPLE 31

Preparation of:

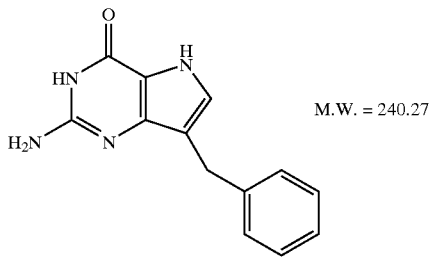

M.W. = 240.27

2-Amino-7-(phenylmethyl)-4-oxo-3H,5H-pyrrolo[3,2-d]pyrimidine

Methyl 3-amino-4-(phenylmethyl)-1H-pyrrole-2-carboxylate, obtained from Example 22 (4.6 g, 20 mmol) was dissolved in dimethylformamide (100 mL) and cooled to 0–5° C. Triethylamine (6.1 g, 60 mmol, 3 eq) was added followed N,N'-bisBOCthiourea (6.1 g, 22 mmol, 1.1 eq) and the solution stirred for 30 minutes. Mercuric chloride (6.0 g, 22 mmol, 1.1 eq) was added, the solution allowed to come to room temperature and stir for 18 hours. The dimethylformamide was removed in vacuo and the remaining solid stirred in water (100 mL) for 40 minutes. The solid was collected by filtration and extracted with hot methanol (150 mL). The extract was concentrated to give a gold-colored syrup (10.1 g). A portion of the syrup (9.4 g) was stirred in trifluoroacetic acid (75 mL) for 18 hours. The volatiles were removed in vacuo and the resulting solid was neutralized with aqueous sodium bicarbonate. The 2-amino-7-(phenylmethyl)-4-oxo-3H,5H-pyrrolo[3,2-d]pyrimidine (2.9 g, 12 mmol, 61%) was collected by filtration. An analytical sample was crystallized from ethanol to give a white solid, which melted with gas evolution at 160° C., resolidified and melted again at 294–296° C.

Analysis: Calc. for $C_{13}H_{12}N_4O$: C, 64.99; H, 5.03; N, 23.32. Found: C, 64.70; H, 4.07; N, 23.11.

EXAMPLE 32

Preparation of:

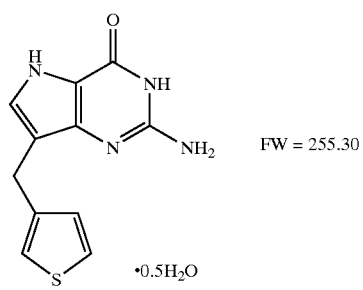

FW = 255.30

•0.5H$_2$O

2-Amino-7-(3-thienylmethyl)-4-oxo-3H,5H-pyrrolo[3,2-d]pyrimidine

Methyl 3-(N,N'-bis-carbomethoxyguanidinyl)-4-(3-thienylmethyl)-1H-pyrrole-2-carboxylate, obtained from Example 23 (3.94 g, 0.01 mol), sodium methoxide (1.62 g, 0.03 mol) and methanol (100 mL) were stirred together and boiled under reflux for six hours. The solvent was evaporated in vacuo and the residue was treated with water (200 mL) containing acetic acid (10 mL). The solid was collected by filtration and crystallized from ethanol to give 2.1 g (85%) of 2-amino-7-(3-thienylmethyl)-4-oxo-3H,5H-pyrrolo[3,2-d]pyrimidine as pale-yellow needles, mp 222–224° C. with gas evolution, followed by resolidification and remelting at 268–270° C. (lit.[1] 271–272° C.).

[1] Montgomery, J. A.; Niwas, S.; Rose, J. D.; Secrist, J. A., III, Babu, Y. S.; Bugg, C. E.; Erion, M. D.; Guida, W. C.; Ealick, S. E., J. Med. Chem., 1993, 58–55.

Analysis: Calc. for $C_{11}H_{10}N_4OS0.5H_2O$: C, 51.75; H, 4.34; N, 21.95. Found: C, 52.11; H, 4.28; N, 21.92.

EXAMPLE 33

Preparation of:

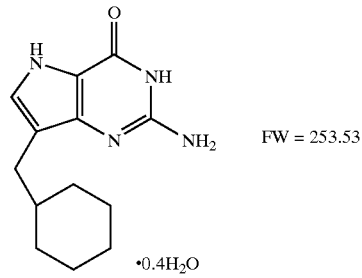

FW = 253.53

•0.4H$_2$O

2-Amino-7-(cyclohexylmethyl-4-oxo-3H,5H-pyrrolo[3,2-d]pyrimidine

Methyl 3-(N,N'-bis-carbomethoxyguanidinyl)-4-(cyclohexylmethyl)-1H-pyrrole-2-carboxylate, obtained from Example 24 (3.94 g, 0.01 mol), methanol (100 mL) and sodium methoxide (1.62 g, 0.03 mol) were stirred together and boiled under reflux for 18 hours. Acetic acid (2 mL) was added and most of the methanol was evaporated in vacuo. The residue was treated with water (200 mL), the solid was collected by filtration and crystallized from methanol as off-white needles, mp>300° C. (1.62 g, 66%).

Analysis: Calc. for $C_{13}H_{18}N_4O0.4H_2O$: C, 61.59; H, 7.48; N, 22.10. Found: C, 61.75; H, 7.33; N, 22.12.

EXAMPLE 34

Preparation of:

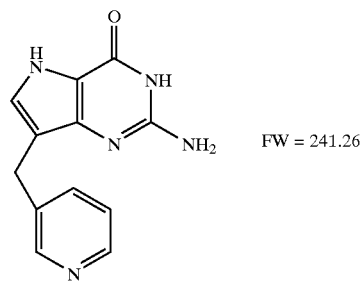

FW = 241.26

2-Amino-7-(3-pyridylmethyl)-4-oxo-3H,5H-pyrrolo[3,2-d]pyrimidine

Methyl 3-(N,N'-bis-carbomethoxyguanidinyl)-4-(3-pyridylmethyl)-1H-pyrrole-2-carboxylate, obtained from Example 26 (15.0 g, 0.04 mol), methanol (100 mL) and sodium hydroxide pellets (3.7 g, 0.9 mol) were stirred together and boiled under reflux for 18 hours. The mixture was cooled, neutralized with acetic acid (5.4 g, 0.09 mol) and the solid collected by filtration. The product was washed in turn with methanol (20 mL), water (200 mL) and methanol (30 mL) and dried at 110° C. overnight to give 8.2 g (88%) of an off-white powder, mp>300° C.

Analysis: Calc. for $C_{12}H_{11}N_5O$: C, 59.74; H, 4.60; N, 29.03. Found: C, 49.53; H, 4.68; N, 28.78.

EXAMPLE 35

Preparation of:

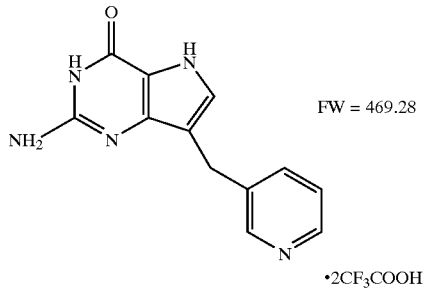

2-Amino-7-(3-pyridylmethyl)-4-oxo-3H,5H-pyrrolo[3,2-d]Pyrimidine bistrifluoroacetate The pyrrole, obtained from Example 25 (1.0 g, 0.002 mol), and trifluoroacetic acid (20 mL) were stirred together overnight at room temperature. The trifluoroacetic acid was evaporated in vacuo and water (20 mL) was added. The solid was collected by filtration, washed with water and dried in air to give 0.7 g (75%) of 2-amino-7-(3-pyridylmethyl)-4-oxo-3H,5H-pyrrolo[3,2-d]pyrimidine bistrifluoroacetate as a white solid, mp>250° C.

Analysis: Calc. for $C_{12}H_{11}N_5O \cdot 2C_2HF_3O_2$: C, 40.95; H, 2.79; N, 14.92. Found: C, 41.00; H, 2.75; N, 14.90.

EXAMPLE 36

Preparation of:

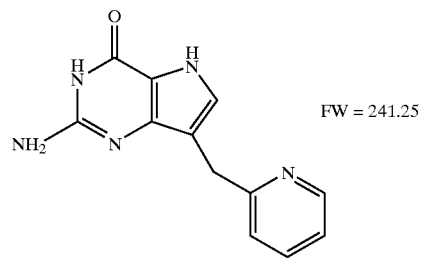

2-Amino-7-[(2-pyridyl)methyl]-4-oxo-3H,5H-pyrrolo[3,2-d]pyrimidine

Methyl 3-amino-4-[2-pyridyl)methyl-1H-pyrrole-2-carboxylate, obtained from Example 17 (1.0 g, 4.32 mmol), N,N'-bis-carbomethoxy-S-methylisothiourea (0.981 g, 4.76 mmol) and triethylamine (1.53 g, 15.13 mmol) were stirred together in acetonitrile (20 mL). Mercuric chloride (1.29 g, 4.76 mmol) was added and an immediate precipitate was observed. The mixture was stirred at room temperature for 16 h. The solvent was evaporated in vacuo, the solid residue washed with water (125 mL) and extracted with hot methanol (125 mL). The methanol was evaporated in vacuo, and the residue crystallized from isopropyl alcohol to give 1.21 g (72%) of product which was used in the next step without further purification.

Methyl-3-(N,N'-bis-carbomethoxyguanidinyl)-4-(phenylmethyl)-1H-pyrrole-2-carboxylate, obtained above (0.92 g, 2.36 mmol), sodium methoxide (0.383 g, 7.08 mmol) and methanol (25 mL) were stirred together and boiled under reflux for 16 h. The solvent was evaporated in vacuo and the residue was treated with water (60 mL) containing acetic acid (2 mL). The solid was collected by filtration and crystallized from hot methanol to give 0.4 g (70%) of 2-amino-7-[(2-pyridyl)methyl]-4-oxo-3H,5H-pyrrolo[3,2-d]pyrimidine as an off-white solid, mp 280–282° C.

Analysis: Calc. for $C_{12}H_{11}N_5O$: C, 59.74; H, 4.60; N, 29.03. Found: C, 59.07; H, 4.65; N, 28.60.

EXAMPLE 37

Preparation of:

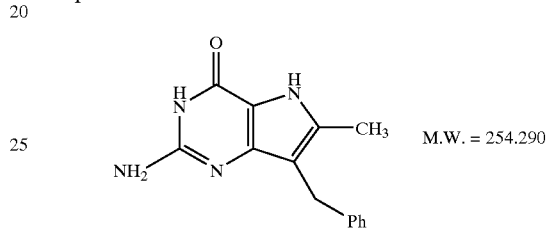

2-Amino-7-phenylmethyl-8-methyl-4-oxo-3H,5H-pyrrolo[3,2-d]pyrimidine

A sample of mixed methyl and ethyl 3-amino-5-methyl-4-(phenylmethyl)pyrrole-2-carboxylate, prepared along the lines of Example 21 (2.45 g, 15.5 mmol), was added to an anhydrous methanol (75 mL) solution containing $ZnCl_2$ (2.32 g, 17 mmol) in one portion. The solution was then stirred for 0.5 h and bis-carbomethoxypseudothiourea, prepared along the lines of Example 27 (3.5 g, 17 mmol) added in two equal portions two hours apart. After the last addition, the mixture was allowed to stir overnight. Thin layer chromatographic analysis ($SiO_2$), ethyl acetate-hexane 1:1) indicated formation of two new lower $R_f$ spots. The mixture was reduced to dryness to give a brown, viscous residue which was stirred for 1 h with a concentrated ammonium hydroxide solution (150 mL). The ammonium hydroxide was decanted from the solution and the residue used directly in the next step.

The residue was dissolved in methanol (75 mL) and treated with NaOH pellets (1.0 g). The mixture was then heated at reflux overnight. The solution was cooled to ambient temperature and the solution carefully neutralized with acetic acid. This produced a thick mixture which was collected by filtration. The cake was washed thoroughly with water to remove inorganic salts. The cake which retained a slight sulfur odor was then dissolved in methanol and treated with charcoal, filtered through Celite and concentrated to give a tan powder. The tan powder was then dissolved in ethyl acetate and passed through a small pad of silica gel with 5% methanol-ethyl acetate as the eluent. The eluent was concentrated yielding a tan powder which was dried in vacuo at acetone reflux for 18 h to give 2-Amino-7-phenylmethyl-8-methyl-4-oxo-3H,5H-pyrrolo[3,2-d]pyrimidine, mp>300° C.(dec).

Analysis: Calc. for $C_{14}H_{14}N_4O$: C, 66.12; H, 5.54; N, 22.03. Found: C, 65.86; H, 5.62; N, 21.82.

EXAMPLE 38

Preparation of:

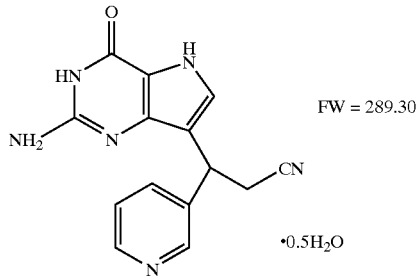

FW = 289.30

·0.5H₂O 3-(3-pyridyl)3-(2-amino-4-oxo-3H,5H-pyrrolo[3,2-d]pyrimidin-yl)propanenitrile hemihydrate Methyl 3-amino-4-[2-cyano-1-(3-pyridyl)ethyl]-1H-pyrrole-2-carboxylate, obtained from Example 19 (2.8 g, 10.36 mmol), N,N'-bis-carbomethoxy-S-methylisothiourea (2.35 g, 11.35 mmol) and triethylamine (3.67 g, 36.26 mmol) were stirred together in acetonitrile (200 mL). Mercuric chloride (3.09 g, 11.39 mmol) was added and an immediate precipitate was observed. The mixture was stirred at room temperature overnight. The solvent was evaporated in vacuo, the solid residue washed with water (2×200 mL) and extracted with hot methanol (200 mL). The methanol was evaporated in vacuo, and the residue crystallized from isopropyl alcohol to give 2.64 g (59.5%) of product which was used in the next step without further purification.

Methyl-3-(N,N'-bis-carbomethoxyguanidinyl)-4-[2-cyano-1-(3-pyridyl)ethyl]-1H-pyrrole-2-carboxylate, obtained above (2.0 g, 4.67 mmol), sodium methoxide (0.757 g 14.00 mmol) and methanol (50 mL) were stirred together and boiled under reflux overnight. The solvent was evaporated in vacuo and the residue was treated with water (120 mL) containing acetic acid (4 mL) and left at room temperature overnight. The precipitated solid was isolated by filtration and crystallized from hot methanol to give 0.36 g (27.5%) of the desired compound as a brown solid, mp 297–299° C. (dec.).

Analysis: Calc. for $C_{14}H_{12}N_6O$:$0.5H_2O$: C, 58.13; H, 4.53; N, 29.05. Found: C, 58.39; H, 4.52; N, 28.70.

EXAMPLE 39

Preparation of:

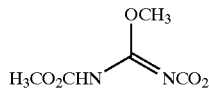

M.W. = 190.153

1,3-Dimethoxycarbonyl-O-methylisourea

Sulfuric acid (112.7 g, 0.97 mol) was added carefully to a cooled CH₃OH (150 mL) solution. In a separate flask, cyanamide (50 g, 1.19 mol) was dissolved in methanol (100 mL) and chilled to ca 5° C. in ice-water. Over 2 h, the MeOH—H₂SO₄ solution was added such that the reaction temperature did not rise above 10° C. After the last addition, the solution was stirred for an additional 1 h and then concentrated in vacuo to give O-methylisourea hydrogen sulfate as a thick-viscous syrup with an assumed quantitative yield which was used directly in the next step.

A three-neck flask fitted with a mechanical stirrer was charged with H₂O (1.1 L), CH₂Cl₂ (1 L) and Na₂CO₃ (254.4 g, 2.4 mol) and the mixture chilled to ca 5° C. To the chilled mixture was then added the O-methylisourea hydrogen sulfate from above, tetrabutylammonium bromide (0.5 g) and methyl chloroformate (556 mL, 7.2 mol). The mixture was stirred vigorously and 25% NaOH (144 g in ca. 600 mL) was added over 0.5 h. After the last addition, the mixture was stirred for an additional 2 h and then filtered through Celite to remove inorganic salts (Na₂SO₄). The layers were separated and the organic layer dried (Na₂SO₄), filtered and concentrated to give the title compound as a thick syrup. The syrup was dried in vacuo overnight during which time it solidified to give 114.7 g (0.6 mol. 53%) of 1,3-dimethoxycarbonyl-O-methylisourea.

EXAMPLE 40

Preparation of:

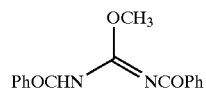

M.W. = 282.418

N,N-Dibenzoylcarbamimidoic acid, methyl ester

O-Methylisourea hydrogen sulfate (17.2 g, 0.1 mol) was suspended in water (100 mL) containing NaOH (20 g, 0.5 mol) and the mixture cooled to 5–10° C. The mixture was stirred vigorously as benzoyl chloride (35.15 g, 0.25 mol) was added at such a rate that the reaction temperature did not rise above 15° C. After the last addition, the mixture was stirred for 3 h and the resulting solid collected by vacuum filtration to give N,N'-dibenzoylcarbamimidoic acid, methyl ester.

EXAMPLE 41

Preparation of:

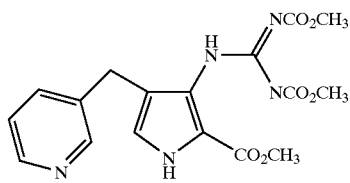

M.W. = 389.365

Methyl 3-[[(methoxycarbonylamino) methoxycarbonylimino]methyl]amino-4-(3-pyridinylmethyl)-1H-pyrrole-2-carboxylate A sample of 3-amino-2-methoxycarbonyl-4-(3-pyridinylmethyl)-1H-pyrrole (2.31 g, 10 mmol) was dissolved in methanol (50 mL) to which was added acetic acid (2.85 mL, 50 mmol) and 1,3-dimethoxycarbonyl-O-methylisourea (2.28 g, 12 mmol) obtained from Example 39. The mixture was allowed to stir overnight at which time TLC (SiO₂, 5% MeOH—CHCl₃) indicated ca 10% remaining starting pyrrole. The mixture was heated at reflux for 2 h after which time the reaction was judged complete by TLC. The mixture was concentrated to dryness and dried in vacuo to remove the last traces of acetic acid to give 3.63 g (9.3 mmol, 93%) of the adduct. An analytical sample was prepared by recrystallization from 2-propanol to give the title compound as a white powder, mp 160–162° C.

IR (KBr) 3299, 1731 and 1701 cm$^{-1}$; MS (m/z) (ES+) 390.2 (100%); $^1$H-NMR (360 MHz, DMSO-d$_6$) 11.81 (br s, D$_2$O exchangeable, 1H), 11.41 (br s, D$_2$O exchangeable, 1H), 9.66 (br s, D$_2$O exchangeable, 1H), 8.33 (m, 2H), 7.50 (d, J=7.7 Hz, 1H), 7.22 (m, 1H), 6.74 (d, J=3.2 Hz, 1H), 3.77 (s, 3H), 3.74 (s, 2H), 3.70 (s, 3H), 3.52 (s, 3H).

Analysis: Calculated for C$_{17}$H$_{19}$N$_5$O$_6$: C, 52.44; H, 4,92; N, 17.98. Found: C, 52.70; H, 4.96; N, 17.91.

EXAMPLE 42

Preparation of:

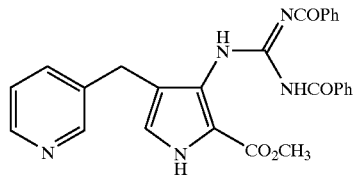

Methyl 3-[[benzoylamino)benzoylimino]methyl] amino-4-(3-pyridinylmethyl)-1H-pyrrole-2-carboxylate A sample of 3-amino-2-methoxycarbonyl-4-(3-pyridinylmethyl)-1H-pyrrole (2.31 g, 10 mmol) was dissolved in methanol (60 mL) to which was added acetic acid (3 6, 50 mmol) and N,N'-dibenzoylcarbamimidoic acid methyl ester (3.38 g, 12 mmol) obtained from Example 40. The mixture was allowed to stir overnight at which time TLC (SiO$_2$, 5% MeOH—CHCl$_3$) indicated ca 70% remaining starting pyrrole and ca 30% adduct at a higher R$_f$. The mixture was heated at reflux for 30 h after which time the reaction was judged complete. The mixture was cooled and the solid collected by vacuum filtration and air-dried overnight to give 3.6 g (7.48 mmol, 74.8%) of the title compound.

EXAMPLE 43

Preparation of:

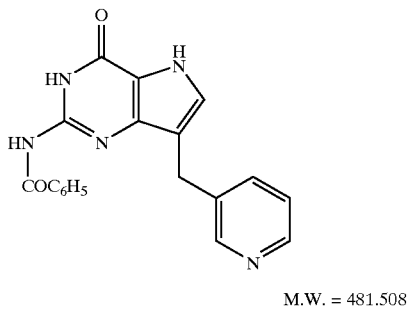

M.W. = 481.508

2)-Benzoylamino-1,5-dihydro-7-(3-pyridinylmethyl)-4H-pyrrolo[3,2-d]pyrimidin-4-one A sample of methyl-3-[[benzoylamino)benzoylimino]methyl]amino-4-(3-pyridinylmethyl)-1H-pyrrole-2-carboxylate (0.962 g, 2 mmol) obtained from Example 42 was suspended in methanol (15 mL). To the stirred suspension was added 25% NaOCH$_3$ (2.6 mL, 12 mmol) in one-portion and immediately the mixture became homogenous. After 3 h, the solution was carefully neutralized with acetic acid and the resulting solid collected by vacuum filtration and washed with water. The filter cake was allowed to dry overnight to give 0.52 g (1.5 mmol, 75%) of the title compound. MS (ES+)M+1 @ 346.4 (100%) and 242.2 (30%).

What is claimed is:

1. A process for producing 9-substituted 9-deazaguanine compound of the formula:

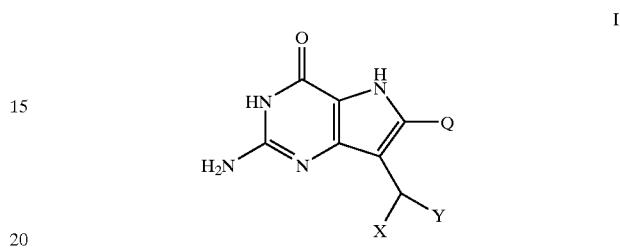

wherein X is a member selected from the group consisting of substituted and unsubstituted aryl, wherein said aryl is selected from the group consisting of phenyl and naphthyl and said substituted aryl contains one or more substituents selected from the group consisting of halogen, C$_{1-3}$ alkyl, C$_{1-3}$ alkoxy, benzyloxy, hydroxyl and trifluoromethyl; 5 and 6 member heterocyclic rings having one N, S, or O atom; alicyclic rings selected from the group consisting of cycloparaffins and cycloolefins having up to 9 carbon atoms; and groups represented by the formula:

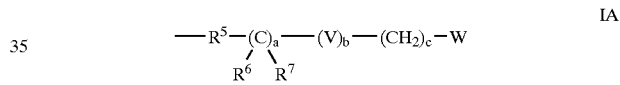

R$^5$ is an optionally substituted cyclic group wherein said cyclic group is selected from the group consisting of aromatic, and alicyclic groups having five to nine atoms and optionally containing one or more heteroatoms selected from the group consisting of O, N and S and wherein said substituted cyclic group is substituted by a member selected from the group consisting of halogen, hydroxyl, alkoxy, alkyl and trifluoromethyl; R$^6$ and R$^7$ are independently H or C$_{1-4}$ alkyl, a is 0–4, b is 0–6, c is 0–1; W is CN, CSNH$_2$, PO(OH)$_2$, COOH, SO$_2$NH$_2$, NH$_2$, OH, CONHNH$_2$, tetrazole, triazole or COR$^8$, said tetrazole and triazole being attached through nitrogen and wherein said R$^8$ is C$_{1-4}$ alkyl, CF$_3$—NH$_2$, or OC$_{1-4}$ alkyl and V is O or NH; Q is a member selected from the group consisting of hydrogen C$_{1-3}$ alkyl, CF$_3$ and phenyl; and which comprises:

1) reacting an aldehyde or ketone represented by the formula:

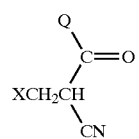

wherein X and Q have the same meanings as defined in formula I with a C$_1$–C$_4$ dialkylaminomalonate to produce an enamine;

2) reacting the enamine obtained from step 1 with a base wherein said base is selected from the group consisting of alkali metal hydroxides, alkaline earth metal hydroxides, sodium hydroxide, sodium amide, pyridine, triethylamine, 1,5-diazabicyclo[4.3.0]non-5-ene and 1,8-diazabicyclo[5.4.0]-undec-7-ene to produce a pyrrole represented by the formula:

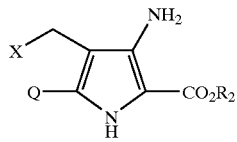

wherein X and Q are defined above and $R_2$ is a $C_1$–$C_4$ alkyl;

3) reacting the pyrrole obtained from step 2 with a compound represented by the formula $R_3OC(O)N=C(Z)NHC(O)OR_3$ wherein $R_3$ is $C_1$–$C_4$ alkyl and Z is S $C_1$–$C_4$ alkyl, SH, Cl or $C_1$–$C_4$ alkoxy to provide a protected guanidine compound represented by the formula:

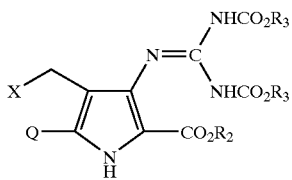

or reacting the pyrrole obtained from step 2 with a derivative of carbamimidoic acid having the formula

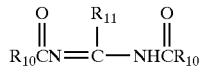

wherein $R_{10}$ is a member selected from the group consisting of phenyl and substituted phenyl and $R_{11}$ is a $C_1$–$C_4$ alkoxy group, to provide a protected guanidine compound represented by the formula:

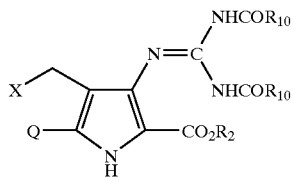

4) reacting the protected guanidine compound from step 3 with 1) trifluoracetic acid or 2) $C_1$–$C_4$ alkoxide or alkali metal or alkaline earth metal hydroxide followed by neutralization with an acid to provide the desired compound of formula I.

2. The process of claim 1 wherein said dialkylaminomalonate is diethylaminomalonate.

3. The process of claim 1 wherein step 1 is carried out in water or water and alcohol mixture.

4. The process of claim 1 wherein step 2 is carried out in the presence of a $C_1$–$C_4$ alcohol mixture.

5. The process of claim 4 wherein said alcohol is methanol.

6. The process of claim 1 wherein step 3 is carried out in the presence of a metal salt.

7. The process of claim 1 wherein said protected guanidino compound is reacted with trifluoroacetic acid.

8. The process of claim 1 wherein said protected guanidino compound is reacted with a member selected from the group consisting $C_1$–$C_4$ alkoxide, alkali metal hydroxide and alkaline earth metal hydroxide, followed by neutralization with an acid.

9. The process of claim 8 wherein the reaction with said member is carried out in alcohol under reflux.

10. The process of claim 1 wherein step 3 is carried out employing a urea compound wherein Z is a $C_{1-4}$ alkoxy group.

11. The process of claim 10 wherein said urea compound is 1,3 dimethoxycarbonyl-O-methylisourea.

12. The process of claim 1 wherein step 3 is carried out employing a derivative of carbamimidoic acid.

13. The process of claim 12 wherein said derivative of carbamimidoic acid is N,N-dibenzoylcarbamimidoic acid, methyl ester.

* * * * *